United States Patent
Wang et al.

(10) Patent No.: US 8,907,155 B2
(45) Date of Patent: Dec. 9, 2014

(54) BIODEGRADABLE AND FLUSHABLE MULTI-LAYERED FILM

(75) Inventors: James H. Wang, Appleton, WI (US); Bo Shi, Neenah, WI (US); Peter Shawn Lortscher, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 100 days.

(21) Appl. No.: 12/949,860

(22) Filed: Nov. 19, 2010

(65) Prior Publication Data

US 2012/0130331 A1    May 24, 2012

(51) Int. Cl.
*A61F 13/15* (2006.01)
*B32B 27/32* (2006.01)
(Continued)

(52) U.S. Cl.
CPC .............. *A61F 13/51478* (2013.01); *B23B 5/04* (2013.01); *B23B 2555/02* (2013.01); *B32B 25/10* (2013.01); *B32B 5/022* (2013.01); *B32B 3/266* (2013.01); *B32B 5/26* (2013.01); *B32B 27/12* (2013.01)
USPC .......................................... 604/364; 442/398

(58) Field of Classification Search
USPC .................. 604/358, 364, 367, 370, 385.101; 442/394, 398
See application file for complete search history.

(56) References Cited

U.S. PATENT DOCUMENTS

| 3,071,485 A | 1/1963 | Wurzburg et al. |
| 3,243,308 A | 3/1966 | Barger et al. |

(Continued)

FOREIGN PATENT DOCUMENTS

| DE | 19802718 A1 | 7/1999 |
| EP | 0062495 A2 | 10/1982 |

(Continued)

OTHER PUBLICATIONS

ASTM D 1238-04c—Standard Test Method for Melt Flow Rates of Thermoplastics by Extrusion Plastomer, Current edition approved Dec. 1, 2004, originally approved in 1965.

(Continued)

*Primary Examiner* — Lynne Anderson
*Assistant Examiner* — Bradley Phillips
(74) *Attorney, Agent, or Firm* — Dority & Manning, P.A.

(57) ABSTRACT

A film that is both biodegradable and flushable, and yet can still act as a barrier to water or other fluids during use, is provided. More particularly, the film contains a water-dispersible core layer that helps the film to lose its integrity after being flushed, as well as a water-barrier skin layer that helps maintain the integrity of the film during use. The nature and relative concentration of the components in the water-barrier layer are selectively controlled to achieve a combination of different functions. That is, the majority of the polymers employed in the water-barrier layer are biodegradable polymers that can be degraded by microorganisms while in an aqueous environment (e.g., septic tank, water treatment facility, etc.). To even further enhance the overall renewability of the layer, a relatively high amount of the biodegradable polymers are starch polymers, which are also renewable. The starch polymers can also minimize the degree of stickiness in the film, which can sometimes result from certain types of synthetic polymers. Even at a high starch content, the present inventors have discovered that films may still be readily formed by using synthetic biodegradable polyesters in combination with the starch to facilitate melt processing.

23 Claims, 2 Drawing Sheets

(51) Int. Cl.
   *B32B 27/12* (2006.01)
   *B23B 5/04* (2006.01)
   *B32B 25/10* (2006.01)
   *A61F 13/514* (2006.01)
   *B32B 5/02* (2006.01)
   *B32B 3/26* (2006.01)
   *B32B 5/26* (2006.01)

(56) References Cited

U.S. PATENT DOCUMENTS

| | | |
|---|---|---|
| 3,354,506 A | 11/1967 | Raley |
| 3,575,173 A | 4/1971 | Loyer |
| 3,650,649 A | 3/1972 | Schippers |
| 3,801,429 A | 4/1974 | Schrenk et al. |
| 4,333,464 A | 6/1982 | Nakano |
| 4,499,154 A | 2/1985 | James et al. |
| 4,503,098 A | 3/1985 | Potts |
| 4,789,699 A | 12/1988 | Kieffer et al. |
| 4,798,603 A | 1/1989 | Meyer et al. |
| 4,801,494 A | 1/1989 | Datta et al. |
| 4,886,512 A | 12/1989 | Damico et al. |
| 4,908,026 A | 3/1990 | Sukiennik et al. |
| 4,964,857 A | 10/1990 | Osborn |
| 5,073,455 A | 12/1991 | Nose et al. |
| 5,106,890 A | 4/1992 | Maruhashi et al. |
| 5,196,247 A | 3/1993 | Wu et al. |
| 5,217,803 A | 6/1993 | McBride et al. |
| 5,219,646 A | 6/1993 | Gallagher et al. |
| 5,248,309 A | 9/1993 | Serbiak et al. |
| 5,254,607 A | 10/1993 | McBride et al. |
| 5,292,783 A | 3/1994 | Buchanan et al. |
| 5,300,358 A | 4/1994 | Evers |
| 5,346,936 A | 9/1994 | Buehler et al. |
| 5,350,354 A | 9/1994 | Billmers |
| 5,405,564 A | 4/1995 | Stepto et al. |
| 5,412,005 A | 5/1995 | Bastioli et al. |
| 5,415,643 A | 5/1995 | Kolb |
| 5,416,181 A | 5/1995 | Nguyen et al. |
| 5,417,679 A | 5/1995 | Toms et al. |
| 5,436,078 A | 7/1995 | Bühler et al. |
| 5,446,079 A | 8/1995 | Buchanan et al. |
| 5,452,981 A | 9/1995 | Crorey et al. |
| 5,462,981 A | 10/1995 | Bastioli et al. |
| 5,506,277 A | 4/1996 | Griesbach, III |
| 5,509,913 A | 4/1996 | Yeo |
| 5,525,281 A | 6/1996 | Lörcks et al. |
| 5,558,659 A | 9/1996 | Sherrod et al. |
| 5,559,171 A | 9/1996 | Buchanan et al. |
| 5,565,509 A | 10/1996 | Nguyen et al. |
| 5,580,911 A | 12/1996 | Buchanan et al. |
| 5,599,293 A | 2/1997 | Orenga et al. |
| 5,599,858 A | 2/1997 | Buchanan et al. |
| 5,649,916 A | 7/1997 | DiPalma et al. |
| 5,662,731 A | 9/1997 | Anderson et al. |
| 5,665,786 A | 9/1997 | Xu et al. |
| 5,679,145 A | 10/1997 | Anderson et al. |
| 5,681,299 A | 10/1997 | Brown |
| 5,695,868 A | 12/1997 | McCormack |
| 5,700,553 A | 12/1997 | Cohen et al. |
| 5,722,966 A | 3/1998 | Christon et al. |
| 5,759,569 A | 6/1998 | Hird et al. |
| 5,817,721 A | 10/1998 | Warzelhan et al. |
| 5,823,988 A | 10/1998 | Orenga et al. |
| 5,855,999 A | 1/1999 | McCormack |
| 5,873,871 A | 2/1999 | Lavash et al. |
| 5,900,322 A | 5/1999 | Buchanan et al. |
| 5,916,678 A | 6/1999 | Jackson et al. |
| 5,916,969 A | 6/1999 | Wang et al. |
| 5,932,497 A | 8/1999 | Morman et al. |
| 5,945,480 A | 8/1999 | Wang et al. |
| 5,948,710 A | 9/1999 | Pomplun et al. |
| 5,952,433 A | 9/1999 | Wang et al. |
| 5,981,012 A | 11/1999 | Pomplun et al. |
| 5,985,396 A | 11/1999 | Kerins et al. |
| 5,997,981 A | 12/1999 | McCormack et al. |
| 6,011,092 A | 1/2000 | Seppälä et al. |
| 6,015,764 A | 1/2000 | McCormack et al. |
| 6,075,118 A | 6/2000 | Wang et al. |
| 6,075,179 A | 6/2000 | McCormack et al. |
| 6,096,809 A | 8/2000 | Lorcks et al. |
| 6,110,158 A | 8/2000 | Kielpikowski |
| 6,111,163 A | 8/2000 | McCormack et al. |
| 6,117,438 A | 9/2000 | Topolkaraev |
| 6,160,199 A | 12/2000 | Noda |
| 6,214,907 B1 | 4/2001 | Tomka |
| 6,231,970 B1 | 5/2001 | Anderson et al. |
| 6,235,816 B1 | 5/2001 | Lorcks et al. |
| 6,258,427 B1 | 7/2001 | Kerins et al. |
| 6,258,924 B1 | 7/2001 | Warzelhan et al. |
| 6,288,184 B1 | 9/2001 | Wilson, Jr. et al. |
| 6,294,238 B1 | 9/2001 | Pomplun et al. |
| 6,296,914 B1 | 10/2001 | Kerins et al. |
| 6,309,736 B1 | 10/2001 | McCormack et al. |
| 6,312,756 B1 | 11/2001 | Dudacek et al. |
| 6,348,524 B2 * | 2/2002 | Bastioli et al. ............... 524/47 |
| 6,380,445 B1 | 4/2002 | Rietz et al. |
| 6,387,528 B1 | 5/2002 | Pomplun et al. |
| 6,432,095 B1 | 8/2002 | Wada et al. |
| 6,461,457 B1 | 10/2002 | Taylor et al. |
| 6,472,497 B2 | 10/2002 | Loercks et al. |
| 6,479,105 B2 | 11/2002 | Chang et al. |
| 6,489,533 B2 | 12/2002 | Imai et al. |
| 6,495,080 B1 | 12/2002 | Tsai et al. |
| 6,511,465 B1 | 1/2003 | Freiburger et al. |
| 6,514,602 B1 * | 2/2003 | Zhao et al. ............... 428/212 |
| 6,515,054 B1 | 2/2003 | Matsushita et al. |
| 6,530,910 B1 | 3/2003 | Pomplun et al. |
| 6,531,642 B2 | 3/2003 | Kurata et al. |
| 6,534,610 B1 | 3/2003 | Wilson, Jr. et al. |
| 6,552,162 B1 | 4/2003 | Wang et al. |
| 6,563,399 B2 | 5/2003 | Love |
| 6,564,399 B1 | 5/2003 | Teal |
| 6,569,137 B2 | 5/2003 | Suzuki et al. |
| 6,573,340 B1 | 6/2003 | Khemani et al. |
| 6,586,354 B1 | 7/2003 | Topolkaraev et al. |
| 6,607,819 B2 | 8/2003 | Wang et al. |
| 6,616,787 B2 | 9/2003 | Imai et al. |
| 6,638,603 B1 | 10/2003 | Kerins et al. |
| 6,663,611 B2 | 12/2003 | Blaney et al. |
| 6,664,333 B2 | 12/2003 | Wang et al. |
| 6,716,203 B2 | 4/2004 | Sorebo et al. |
| 6,747,186 B2 | 6/2004 | Shimizu |
| 6,783,826 B2 | 8/2004 | Sherrod et al. |
| 6,824,734 B2 | 11/2004 | Boggs et al. |
| 6,833,488 B2 | 12/2004 | Bucevschi et al. |
| 6,888,044 B2 | 5/2005 | Fell et al. |
| 6,890,872 B2 | 5/2005 | Bond et al. |
| 6,890,989 B2 | 5/2005 | Wang et al. |
| 6,897,168 B2 | 5/2005 | Branham et al. |
| 6,908,966 B2 | 6/2005 | Chang et al. |
| 6,946,506 B2 | 9/2005 | Bond et al. |
| 6,958,371 B1 | 10/2005 | Wang et al. |
| 6,960,371 B2 | 11/2005 | Bunyard et al. |
| 6,989,193 B2 | 1/2006 | Haile et al. |
| 6,994,865 B2 | 2/2006 | Branham et al. |
| 7,012,116 B1 | 3/2006 | Schertz et al. |
| 7,077,994 B2 | 7/2006 | Bond et al. |
| 7,094,817 B2 | 8/2006 | Halley et al. |
| 7,098,292 B2 | 8/2006 | Zhao et al. |
| 7,153,569 B2 | 12/2006 | Kaufman et al. |
| 7,176,251 B1 | 2/2007 | Bastioli et al. |
| 7,179,245 B2 | 2/2007 | Giori |
| 7,214,414 B2 | 5/2007 | Khemani et al. |
| 7,297,394 B2 | 11/2007 | Khemani et al. |
| 7,517,339 B2 | 4/2009 | Pedersen et al. |
| 7,619,132 B2 | 11/2009 | Topolkaraev et al. |
| 7,727,209 B2 | 6/2010 | Mizutani et al. |
| 7,776,020 B2 | 8/2010 | Kaufman et al. |
| 7,902,094 B2 | 3/2011 | Haile et al. |
| 7,928,180 B2 | 4/2011 | Shimoda et al. |
| 2002/0028857 A1 | 3/2002 | Holy |
| 2002/0042599 A1 | 4/2002 | Zhao et al. |
| 2002/0111596 A1 | 8/2002 | Fletcher et al. |

(56) References Cited

U.S. PATENT DOCUMENTS

| | | |
|---|---|---|
| 2002/0127385 A1 | 9/2002 | Topolkaraev et al. |
| 2003/0108701 A1* | 6/2003 | Bond et al. .................. 428/35.7 |
| 2003/0116462 A1 | 6/2003 | Sorebo et al. |
| 2004/0060112 A1 | 4/2004 | Fell et al. |
| 2004/0122135 A1* | 6/2004 | Halley et al. .................. 524/47 |
| 2004/0122403 A1 | 6/2004 | Mitchler et al. |
| 2004/0225269 A1* | 11/2004 | Zhao et al. .................. 604/364 |
| 2004/0267217 A1 | 12/2004 | Dave et al. |
| 2005/0245162 A1 | 11/2005 | McCormack et al. |
| 2005/0282456 A1 | 12/2005 | Zhao et al. |
| 2006/0149199 A1 | 7/2006 | Topolkaraev et al. |
| 2007/0241483 A1* | 10/2007 | Bastioli et al. ................ 264/555 |
| 2007/0264460 A1 | 11/2007 | Del Tredici |
| 2008/0147034 A1 | 6/2008 | Wang |
| 2009/0018516 A1 | 1/2009 | Kelly |
| 2009/0054548 A1* | 2/2009 | Wang et al. .................. 523/111 |
| 2009/0084321 A1 | 4/2009 | Mo |
| 2009/0286031 A1 | 11/2009 | Shi et al. |

FOREIGN PATENT DOCUMENTS

| | | |
|---|---|---|
| EP | 0062495 A3 | 10/1982 |
| EP | 0327505 A2 | 8/1989 |
| EP | 0327505 A3 | 8/1989 |
| EP | 0417828 A1 | 3/1991 |
| EP | 0809680 B1 | 12/1997 |
| EP | 0947559 A2 | 10/1999 |
| EP | 0947559 A3 | 10/1999 |
| EP | 1116748 A1 | 7/2001 |
| JP | 9143893 A | 6/1997 |
| WO | WO 8203324 A1 | 10/1982 |
| WO | WO 9114413 A1 | 10/1991 |
| WO | WO 9202199 A1 | 2/1992 |
| WO | WO 9620831 A1 | 7/1996 |
| WO | WO 2005116118 A1 | 12/2005 |

OTHER PUBLICATIONS

ASTM D 3418 03 (D 3417-99)—Standard Test Method for Enthalpies of Fusion and Crystallization of Polymers by Differential Scanning Calorimetry, Current edition approved Dec. 1, 2003, originally approved in 1975.

ASTM 5034 95—Standard Test Method for Breaking Strength and Elongation of Textile Fabrics (Grab Test), Current edition approved May 15, 1995.

ASTM D 5338 92—Standard Test Method for Determining Aerobic Biodegradation of Plastic Materials Under Controlled Composting Conditions, Current edition approved Dec. 15, 1992.

Technical Information for BIOPLAST GF 106/02 provided by BIOTEC, 4 pages.

Search Report and Written Opinion for PCT/IB2011/054597 dated May 21, 2012, 12 pages.

* cited by examiner

BIODEGRADABLE AND FLUSHABLE MULTI-LAYERED FILM

BACKGROUND OF THE INVENTION

Disposable absorbent articles are currently used in many different applications, including diapers and training pants for infants and children, feminine care products such as sanitary napkins or tampons, adult incontinence products, and health care products such as surgical drapes or wound dressings. The disposable absorbent article usually comprises a topsheet, a backsheet and an absorbent core positioned between the backsheet and the topsheet. Depending on the type of use involved, disposable absorbent articles can be subjected to one or more insults from aqueous liquids such as water, urine, menses or blood. As a result, the backsheet materials of these disposable products are typically made of liquid impermeable materials, such as polypropylene or polyethylene films, which exhibit sufficient strength and handling capability so that the disposable absorbent article retains its integrity during use by the wearer and does not allow leakage of the liquid from the product.

Many disposable absorbent articles can be difficult to dispose of into an aqueous environment. For example, attempts to flush many disposable absorbent articles down the toilet can cause blockage of the toilet or pipes connecting the toilet to the sewage system. In particular, the backsheet materials used in these disposable absorbent articles generally do not dissolve, disintegrate or disperse readily when flushed down a toilet so that the disposable absorbent article cannot be disposed of in this manner. If the backsheet materials are made very thin to reduce the overall bulk of the disposable absorbent article and reduce the likelihood of blockage of the toilet or sewage pipe, it may not exhibit sufficient strength to prevent tearing or ripping as the material is subjected to the stresses of normal use by the wearer. In a number of instances, it would be desirable to be able to flush these disposable absorbent articles down the toilet. These include certain catamenial products, known as labial or interlabial sanitary napkins or pads. Interlabial pads have the potential to provide greater freedom from inconvenience because of their small size and reduced risk of leakage. Indeed, these interlabial pads are small enough to be easily flushed down the toilet, typically without clogging it or the sewage pipes. Even though flushable, such products could put a significant environmental demand on sewage treatment or septic tank systems if they are not readily susceptible to degradation and disintegration after being flushed.

Various attempts have therefore been made to solve this problem. For example, U.S. Pat. No. 6,514,602 to Zhao, et al. describes a water-flushable film that contains a water-impervious biodegradable layer and a water-dispersible layer. The biodegradable layer includes from 65% to 100% of a water-insoluble biodegradable thermoplastic polymer and from 0% to 30% of a water-soluble thermoplastic polymer, and the water-dispersible layer contains from 60% to 100% of a water-soluble thermoplastic polymer and from 0 to 40% of a water-insoluble thermoplastic polymer. In one example, the film contains a $1^{st}$ layer of 25% Bionolle (polybutylene succinate adiapte copolymer) and 75% PEO; a $2^{nd}$ layer of 25% Bionolle and 75% PEO; and a $3^{rd}$ layer of 100% Bionolle. Despite imparting some barrier properties to the film, various problems nevertheless remain with such films. For instance, several of the synthetic biodegradable polymers employed in Zhao, et al. can lead to an undesirable stickiness when dry or wet, as well as relatively poor mechanical properties. The polymers are also expensive. Furthermore, while the synthetic biodegradable polymers employed therein can be melt processed, they are not generally renewable, which limits the overall renewability of the film. Unfortunately, polymers that are both biodegradable and renewable are often difficult to melt process into a film.

As such, a need currently exists for a flushable and biodegradable film that has good mechanical properties, and yet is able to employ at least some renewable components.

SUMMARY OF THE INVENTION

In accordance with one embodiment of the present invention, an absorbent article is disclosed that comprises a liquid permeable topsheet, a generally liquid impermeable backsheet, and an absorbent core positioned between the backsheet and the topsheet. The backsheet includes a biodegradable and flushable film that comprises a water-dispersible core layer and a water-barrier skin layer positioned adjacent to the water-dispersible core layer. The core layer constitutes from about 50 wt. % to about 99 wt. % of the film. The water-dispersible layer comprises a water-soluble polymer, and the skin layer is formed from biodegradable polymers. From about 10 wt. % to about 60 wt. % of the biodegradable polymers are starch polymers and from about 40 wt. % to about 90 wt. % of the biodegradable polymers are synthetic biodegradable polyesters.

In accordance with another embodiment of the present invention, a biodegradable and flushable film is disclosed that has a thickness of about 50 micrometers or less. The film comprises a water-dispersible core layer and a water-barrier skin layer positioned adjacent to the water-dispersible core layer. The core layer constitutes from about 50 wt. % to about 99 wt. % of the film and the skin layer constitutes from about 1 wt. % to about 50 wt. % of the film. The water-dispersible layer comprises a water-soluble polymer. Biodegradable polymers constitute from about 80 wt. % to 100 wt. % of the polymer content of the water-barrier layer, and from about 10 wt. % to about 60 wt. % of the biodegradable polymers are starch polymers and from about 40 wt. % to about 90 wt. % of the biodegradable polymers are synthetic biodegradable polyesters.

Other features and aspects of the present invention are discussed in greater detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which.

Figure 1:
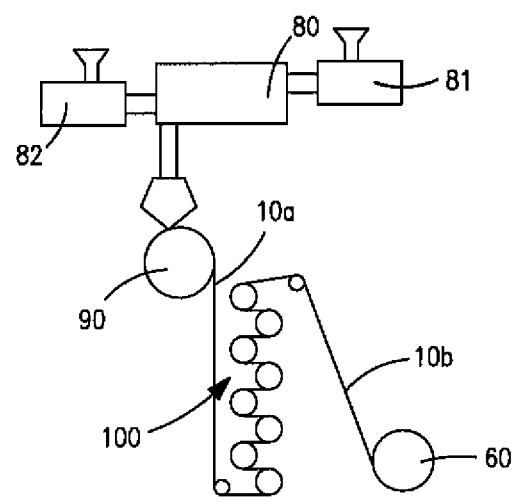
FIG. 1 is a schematic illustration of one embodiment of a method for forming the film of the present invention.

Repeat use of references characters in the present specification and drawings is intended to represent same or analogous features or elements of the invention.

DETAILED DESCRIPTION OF REPRESENTATIVE EMBODIMENTS

Definitions

As used herein, the term "biodegradable" generally refers to a material that degrades from the action of naturally occur-ring microorganisms, such as bacteria, fungi, and algae; environmental heat; moisture; or other environmental factors. The degree of degradation may be determined according to ASTM Test Method 5338.92.

DETAILED DESCRIPTION

Reference now will be made in detail to various embodiments of the invention, one or more examples of which are set forth below. Each example is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention covers such modifications and variations as come within the scope of the appended claims and their equivalents.

Generally speaking, the present invention is directed to a film that is both biodegradable and flushable, and yet can still act as a barrier to water or other fluids during use. More particularly, the film contains a water-dispersible core layer that helps the film to lose its integrity after being flushed, as well as a water-barrier skin layer that helps maintain the integrity of the film during use. According to the present invention, the nature and relative concentration of the components in the water-barrier layer are selectively controlled to achieve a combination of different functions. That is, the majority of the polymers employed in the water-barrier layer are biodegradable polymers that can be degraded by microorganisms while in an aqueous environment (e.g., septic tank, wastewater treatment facility, etc.). To even further enhance the overall renewability of the layer, a relatively high amount of the biodegradable polymers are starch polymers, which are also renewable. The starch polymers can also minimize the degree of stickiness in the film, which can sometimes result from certain types of synthetic polymers. Even at a high starch content, the present inventors have discovered that films may still be readily formed by using synthetic biodegradable polyesters in combination with the starch to facilitate melt processing. Various embodiments of the film layers, as well as the use of the film in certain articles, will now be described in more detail.

I. Water-Barrier Skin Layer

The water-barrier layer of the film is substantially liquid impermeable such that it will effectively limit the flow of liquids therethrough during the time in which it is in use. When the film is employed in an absorbent article, for example, the water-barrier layer may inhibit bodily fluids (e.g., urine) from escaping through the film and contacting the body.

As indicated above, the polymers used to form the water-barrier layer are generally biodegradable in nature. For example, in some embodiments, biodegradable polymers may constitute from about 70 wt. % to 100 wt. %, in some embodiments from about 80 wt. % to 100 wt. %, and in some embodiments, from about 90 wt. % to about 99 wt. % of the polymer content of the water-barrier layer. With respect to such polymers, the relative proportion of synthetic biodegradable polyesters and starch polymers is also controlled to achieve a balance between renewability and melt processability. More specifically, of the biodegradable polymers employed in the water-barrier layer, from about 10 wt. % to about 60 wt. %, in some embodiments from about 15 wt. % to about 55 wt. %, and in some embodiments, from about 20 wt. % to about 50 wt. % are typically starch polymers. Likewise, the synthetic biodegradable polyesters typically constitute from about 40 wt. % to about 90 wt. %, in some embodiments from about 45 wt. % to about 85 wt. %, and in some embodiments, from about 50 wt. % to about 80 wt. % of the biodegradable polymers. It should be understood that the weight of starch referenced herein includes any bound water that naturally occurs in the starch before mixing it with other components. Starches, for instance, may have a bound water content of about 5% to 16% by weight of the starch.

A. Starch Polymer

Although starch polymers are produced in many plants, typical sources includes seeds of cereal grains, such as corn, waxy corn, wheat, sorghum, rice, and waxy rice; tubers, such as potatoes; roots, such as tapioca (i.e., cassava and manioc), sweet potato, and arrowroot; and the pith of the sago palm. Broadly speaking, any native (unmodified) and/or modified starch (e.g., chemically or enzymatically modified) may be employed in the present invention. Chemically modified starches are particularly desirable in certain embodiments as they typically possess a higher degree of water sensitivity, and therefore can help facilitate degradation upon flushing of the film. Such chemically modified starches may be obtained through typical processes known in the art (e.g., esterification, etherification, oxidation, acid hydrolysis, enzymatic hydrolysis, etc.). Starch ethers and/or esters may be particularly desirable, such as hydroxyalkyl starches, carboxymethyl starches, etc. The hydroxyalkyl group of hydroxylalkyl starches may contain, for instance, 2 to 10 carbon atoms, in some embodiments from 2 to 6 carbon atoms, and in some embodiments, from 2 to 4 carbon atoms. Representative hydroxyalkyl starches such as hydroxyethyl starch, hydroxypropyl starch, hydroxybutyl starch, and derivatives thereof. Starch esters, for instance, may be prepared using a wide variety of anhydrides (e.g., acetic, propionic, butyric, and so forth), organic acids, acid chlorides, or other esterification reagents. The degree of esterification may vary as desired, such as from 1 to 3 ester groups per glucosidic unit of the starch.

The starch polymer may contain different weight percentages of amylose and amylopectin, different polymer molecular weights, etc. High amylose starches contain greater than about 50% by weight amylose and low amylose starches contain less than about 50% by weight amylose. Although not required, low amylose starches having an amylose content of from about 10% to about 40% by weight, and in some embodiments, from about 15% to about 35% by weight, are particularly suitable for use in the present invention. Examples of such low amylose starches include corn starch and potato starch, both of which have an amylose content of approximately 20% by weight. Particularly suitable low amylose starches are those having a number average molecular weight ("$M_n$") ranging from about 50,000 to about 1,000,000 grams per mole, in some embodiments from about 75,000 to about 800,000 grams per mole, and in some embodiments, from about 100,000 to about 600,000 grams per mole, and/or a weight average molecular weight ("$M_w$") ranging from about 5,000,000 to about 25,000,000 grams per mole, in some embodiments from about 5,500,000 to about 15,000,000 grams per mole, and in some embodiments, from about 6,000,000 to about 12,000,000 grams per mole. The ratio of the weight average molecular weight to the number average molecular weight ("$M_w/M_n$"), i.e., the "polydispersity index", is also relatively high. For example, the polydispersity index may range from about 10 to about 100, and in some embodiments, from about 20 to about 80. The weight and number average molecular weights may be determined by methods known to those skilled in the art.

B. Synthetic Biodegradable Polyester

The biodegradable polyesters employed in the present invention typically have a relatively low glass transition temperature ("$T_g$") to reduce stiffness of the film and improve the processability of the polymers. For example, the $T_g$ may be about 25° C. or less, in some embodiments about 0° C. or less, and in some embodiments, about −10° C. or less. Likewise, the melting point of the biodegradable polyesters is also relatively low to improve the rate of biodegradation. For example, the melting point is typically from about 50° C. to about 180° C., in some embodiments from about 80° C. to about 160° C., and in some embodiments, from about 100° C. to about 140° C. The melting temperature and glass transition temperature may be determined using differential scanning calorimetry ("DSC") in accordance with ASTM D-3417 as is well known in the art. Such tests may be employed using a DSC Q100 Differential Scanning calorimeter (outfitted with a liquid nitrogen cooling accessory) and with a THERMAL ADVANTAGE (release 4.6.6) analysis software program, which are available from T.A. Instruments Inc. of New Castle, Del.

The biodegradable polyesters may also have a number average molecular weight ("$M_n$") ranging from about 40,000 to about 120,000 grams per mole, in some embodiments from about 50,000 to about 100,000 grams per mole, and in some embodiments, from about 60,000 to about 85,000 grams per mole. Likewise, the polyesters may also have a weight average molecular weight ("$M_w$") ranging from about 70,000 to about 300,000 grams per mole, in some embodiments from about 80,000 to about 200,000 grams per mole, and in some embodiments, from about 100,000 to about 150,000 grams per mole. The ratio of the weight average molecular weight to the number average molecular weight ("$M_w/M_n$"), i.e., the "polydispersity index", is also relatively low. For example, the polydispersity index typically ranges from about 1.0 to about 4.0, in some embodiments from about 1.2 to about 3.0, and in some embodiments, from about 1.4 to about 2.0. The weight and number average molecular weights may be determined by methods known to those skilled in the art.

The biodegradable polyesters may also have an apparent viscosity of from about 100 to about 1000 Pascal seconds (Pa·s), in some embodiments from about 200 to about 800 Pa·s, and in some embodiments, from about 300 to about 600 Pa·s, as determined at a temperature of 170° C. and a shear rate of 1000 sec$^{-1}$. The melt flow index of the biodegradable polyesters may also range from about 0.1 to about 30 grams per 10 minutes, in some embodiments from about 0.5 to about 10 grams per 10 minutes, and in some embodiments, from about 1 to about 5 grams per 10 minutes. The melt flow index is the weight of a polymer (in grams) that may be forced through an extrusion rheometer orifice (0.0825-inch diameter) when subjected to a load of 2160 grams in 10 minutes at a certain temperature (e.g., 190° C.), measured in accordance with ASTM Test Method D1238-E.

Of course, the melt flow index of the biodegradable polyesters will ultimately depend upon the selected film-forming process. For example, when extruded as a cast film, higher melt flow index polymers are typically desired, such as about 4 grams per 10 minutes or more, in some embodiments, from about 5 to about 12 grams per 10 minutes, and in some embodiments, from about 7 to about 9 grams per 10 minutes. Likewise, when formed as a blown film, lower melt flow index polymers are typically desired, such as less than about 12 grams per 10 minutes or less, in some embodiments from about 1 to about 7 grams per 10 minutes, and in some embodiments, from about 2 to about 5 grams per 10 minutes.

Examples of suitable biodegradable polyesters include aliphatic polyesters, such as polycaprolactone, polyesteramides, modified polyethylene terephthalate, polylactic acid (PLA) and its copolymers, terpolymers based on polylactic acid, polyglycolic acid, polyalkylene carbonates (such as polyethylene carbonate), polyhydroxyalkanoates (PHA), poly-3-hydroxybutyrate (PHB), poly-3-hydroxyvalerate (PHV), poly-3-hydroxybutyrate-co-4-hydroxybutyrate, poly-3-hydroxybutyrate-co-3-hydroxyvalerate copolymers (PHBV), poly-3-hydroxybutyrate-co-3-hydroxyhexanoate, poly-3-hydroxybutyrate-co-3-hydroxyoctanoate, poly-3-hydroxybutyrate-co-3-hydroxydecanoate, poly-3-hydroxybutyrate-co-3-hydroxyoctadecanoate, and succinate-based aliphatic polymers (e.g., polybutylene succinate, polybutylene succinate adipate, polyethylene succinate, etc.); aromatic polyesters and modified aromatic polyesters; and aliphatic-aromatic copolyesters. In one particular embodiment, the biodegradable polyester is an aliphatic-aromatic copolyester (e.g., block, random, graft, etc.). The aliphatic-aromatic copolyester may be synthesized using any known technique, such as through the condensation polymerization of a polyol in conjunction with aliphatic and aromatic dicarboxylic acids or anhydrides thereof. The polyols may be substituted or unsubstituted, linear or branched, polyols selected from polyols containing 2 to about 12 carbon atoms and polyalkylene ether glycols containing 2 to 8 carbon atoms. Examples of polyols that may be used include, but are not limited to, ethylene glycol, diethylene glycol, propylene glycol, 1,2-propanediol, 1,3-propanediol, 2,2-dimethyl-1,3-propanediol, 1,2-butanediol, 1,3-butanediol, 1,4-butanediol, 1,2-pentanediol, 1,5-pentanediol, 1,6-hexanediol, polyethylene glycol, diethylene glycol, 2,2,4-trimethyl-1,6-hexanediol, thiodiethanol, 1,3-cyclohexanedimethanol, 1,4-cyclohexanedimethanol, 2,2,4,4-tetramethyl-1,3-cyclobutanediol, cyclopentanediol, triethylene glycol, and tetraethylene glycol. Preferred polyols include 1,4-butanediol; 1,3-propanediol; ethylene glycol; 1,6-hexanediol; diethylene glycol; and 1,4-cyclohexanedimethanol.

Representative aliphatic dicarboxylic acids that may be used include substituted or unsubstituted, linear or branched, non-aromatic dicarboxylic acids selected from aliphatic dicarboxylic acids containing 1 to about 10 carbon atoms, and derivatives thereof. Non-limiting examples of aliphatic dicarboxylic acids include malonic, malic, succinic, oxalic, glutaric, adipic, pimelic, azelaic, sebacic, fumaric, 2,2-dimethyl glutaric, suberic, 1,3-cyclopentanedicarboxylic, 1,4-cyclohexanedicarboxylic, 1,3-cyclohexanedicarboxylic, diglycolic, itaconic, maleic, and 2,5-norbornanedicarboxylic. Representative aromatic dicarboxylic acids that may be used include substituted and unsubstituted, linear or branched, aromatic dicarboxylic acids selected from aromatic dicarboxylic acids containing 8 or more carbon atoms, and derivatives thereof. Non-limiting examples of aromatic dicarboxylic acids include terephthalic acid, dimethyl terephthalate, isophthalic acid, dimethyl isophthalate, 2,6-napthalene dicarboxylic acid, dimethyl-2,6-naphthalate, 2,7-naphthalenedicarboxylic acid, dimethyl-2,7-naphthalate, 3,4'-diphenyl ether dicarboxylic acid, dimethyl-3,4'diphenyl ether dicarboxylate, 4,4'-diphenyl ether dicarboxylic acid, dimethyl-4,4'-diphenyl ether dicarboxylate, 3,4'-diphenyl sulfide dicarboxylic acid, dimethyl-3,4'-diphenyl sulfide dicarboxylate, 4,4'-diphenyl sulfide dicarboxylic acid, dimethyl-4,4'-diphenyl sulfide dicarboxylate, 3,4'-diphenyl sulfone dicarboxylic acid, dimethyl-3,4'-diphenyl sulfone dicarboxylate, 4,4'-diphenyl sulfone dicarboxylic acid, dimethyl-4,4'-diphenyl sulfone dicarboxylate, 3,4'-benzophenonedicarboxylic acid, dimethyl-3,4'-benzophenonedicarboxylate, 4,4'-benzophenonedicarboxylic acid, dimethyl-4,4'-benzophenonedicarboxylate, 1,4-naphthalene dicarboxylic acid, dimethyl-1,4- naphthalate, 4,4'-methylene bis(benzoic acid), dimethyl-4,4'-methylenebis(benzoate), etc., and mixtures thereof.

The polymerization may be performed in the presence of a catalyst, such as a titanium-based catalyst (e.g., tetraisopropyltitanate, tetraisopropoxy titanium, dibutoxydiacetoacetoxy titanium, or tetrabutyltitanate). If desired, a diisocyanate chain extender may be reacted with the copolyester to increase its molecular weight. Representative diisocyanates may include toluene 2,4-diisocyanate, toluene 2,6-diisocyanate, 2,4'-diphenylmethane diisocyanate, naphthylene-1,5-diisocyanate, xylylene diisocyanate, hexamethylene diisocyanate ("HMDI"), isophorone diisocyanate and methylenebis(2-isocyanatocyclohexane). Trifunctional isocyanate compounds may also be employed that contain isocyanurate and/or biurea groups with a functionality of not less than three, or to replace the diisocyanate compounds partially by tri-or polyisocyanates. The preferred diisocyanate is hexamethylene diisocyanate. The amount of the chain extender employed is typically from about 0.3 to about 3.5 wt. %, in some embodiments, from about 0.5 to about 2.5 wt. % based on the total weight percent of the polymer.

The copolyesters may either be a linear polymer or a long-chain branched polymer. Long-chain branched polymers are generally prepared by using a low molecular weight branching agent, such as a polyol, polycarboxylic acid, hydroxy acid, and so forth. Representative low molecular weight polyols that may be employed as branching agents include glycerol, trimethylolpropane, trimethylolethane, polyethertriols, 1,2,4-butanetriol, pentaerythritol, 1,2,6-hexanetriol, sorbitol, 1,1,4,4,-tetrakis (hydroxymethyl)cyclohexane, tris(2-hydroxyethyl) isocyanurate, and dipentaerythritol. Representative higher molecular weight polyols (molecular weight of 400 to 3000) that may be used as branching agents include triols derived by condensing alkylene oxides having 2 to 3 carbons, such as ethylene oxide and propylene oxide with polyol initiators. Representative polycarboxylic acids that may be used as branching agents include hemimellitic acid, trimellitic (1,2,4-benzenetricarboxylic) acid and anhydride, trimesic (1,3,5-benzenetricarboxylic) acid, pyromellitic acid and anhydride, benzenetetracarboxylic acid, benzophenone tetracarboxylic acid, 1,1,2,2-ethane-tetracarboxylic acid, 1,1,2-ethanetricarboxylic acid, 1,3,5-pentanetricarboxylic acid, and 1,2,3,4-cyclopentanetetracarboxylic acid. Representative hydroxy acids that may be used as branching agents include malic acid, citric acid, tartaric acid, 3-hydroxyglutaric acid, mucic acid, trihydroxyglutaric acid, 4-carboxyphthalic anhydride, hydroxyisophthalic acid, and 4-(beta-hydroxyethyl)phthalic acid. Such hydroxy acids contain a combination of 3 or more hydroxyl and carboxyl groups. Especially preferred branching agents include trimellitic acid, trimesic acid, pentaerythritol, trimethylol propane and 1,2,4-butanetriol.

The aromatic dicarboxylic acid monomer constituent may be present in the copolyester in an amount of from about 10 mole % to about 40 mole %, in some embodiments from about 15 mole % to about 35 mole %, and in some embodiments, from about 15 mole % to about 30 mole %. The aliphatic dicarboxylic acid monomer constituent may likewise be present in the copolyester in an amount of from about 15 mole % to about 45 mole %, in some embodiments from about 20 mole % to about 40 mole %, and in some embodiments, from about 25 mole % to about 35 mole %. The polyol monomer constituent may also be present in the aliphatic-aromatic copolyester in an amount of from about 30 mole % to about 65 mole %, in some embodiments from about 40 mole % to about 50 mole %, and in some embodiments, from about 45 mole % to about 55 mole %.

In one particular embodiment, for example, the aliphatic-aromatic copolyester may comprise the following structure:

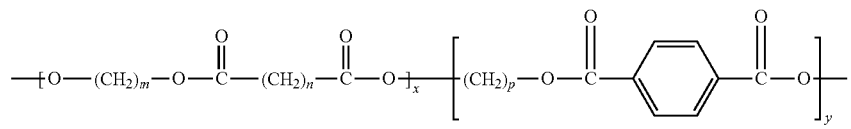

wherein, m is an integer from 2 to 10, in some embodiments from 2 to 4, and in one embodiment, 4;

n is an integer from 0 to 18, in some embodiments from 2 to 4, and in one embodiment, 4;

p is an integer from 2 to 10, in some embodiments from 2 to 4, and in one embodiment, 4;

x is an integer greater than 1; and y is an integer greater than 1. One example of such a copolyester is polybutylene adipate terephthalate, which is commercially available under the designation ECOFLEX® F BX 7011 from BASF Corp. Another example of a suitable copolyester containing an aromatic terephtalic acid monomer constituent is available under the designation ENPOL™ 8060M from IRE Chemicals (South Korea). Other suitable aliphatic-aromatic copolyesters may be described in U.S. Pat. Nos. 5,292,783; 5,446,079; 5,559,171; 5,580,911; 5,599,858; 5,817,721; 5,900,322; and 6,258,924, which are incorporated herein in their entirety by reference thereto for all purposes. Still other suitable biodegradable polyesters are described in U.S. Pat. No. 6,472,497 to Loercks, et al. and U.S. Patent Application Publication No. 2005/0182196 to Khemani, et al., which are incorporated herein in their entirety by reference thereto for all relevant purposes.

C. Other Components

If desired, a plasticizer may also be employed to further enhance the ability of the starch to be melt processed. When employed, the plasticizers typically soften and penetrate into the outer membrane of the starch and cause the inner starch chains to absorb water and swell. This swelling will, at some point, cause the outer shell to rupture and result in an irreversible destructurization of the starch granule. Once destructurized, the starch polymer chains, which are initially compressed within the granules, may stretch out and form a generally disordered intermingling of polymer chains. Upon resolidification, however, the chains may reorient themselves to form crystalline or amorphous solids having varying strengths depending on the orientation of the starch polymer chains.

Suitable plasticizers may include, for instance, polyhydric alcohol plasticizers, such as sugars (e.g., glucose, sucrose, fructose, raffinose, maltodextrose, galactose, xylose, maltose, lactose, mannose, and erythrose), sugar alcohols (e.g., erythritol, xylitol, malitol, mannitol, and sorbitol), polyols (e.g., ethylene glycol, glycerol, propylene glycol, dipropylene glycol, butylene glycol, and hexane triol), etc. Also suitable are hydrogen bond forming organic compounds which do not have hydroxyl group, including urea and urea derivatives; anhydrides of sugar alcohols such as sorbitan; animal proteins such as gelatin; vegetable proteins such as sunflower protein, soybean proteins, cotton seed proteins; and mixtures thereof. Other suitable plasticizers may include phthalate esters, dimethyl and diethylsuccinate and related esters, glycerol triacetate, glycerol mono and diacetates, glycerol mono, di, and tripropionates, butanoates, stearates, lactic acid esters, citric acid esters, adipic acid esters, stearic acid esters, oleic acid esters, and other acid esters. Aliphatic acids may also be used, such as copolymers of ethylene and acrylic acid, polyethylene grafted with maleic acid, polybutadiene-co-acrylic acid, polybutadiene-co-maleic acid, polypropylene-co-acrylic acid, polypropylene-co-maleic acid, and other hydrocarbon based acids. A low molecular weight plasticizer is preferred, such as less than about 20,000 g/mol, preferably less than about 5,000 g/mol and more preferably less than about 1,000 g/mol.

The plasticizer may be incorporated into the water-barrier layer using any of a variety of known techniques. For example, the starch polymers may be "pre-plasticized" prior to incorporation into the film to form what is often referred to as a "thermoplastic starch." The relative amount of the starch and plasticizer employed in the thermoplastic starch may vary depending on a variety of factors, such as the desired molecular weight, the type of starch, the affinity of the plasticizer for the starch, etc. Typically, however, the starch polymer constitutes from about 40 wt. % to about 98 wt. %, in some embodiments from about 50 wt. % to about 95 wt. %, and in some embodiments, from about 60 wt. % to about 90 wt. % of the thermoplastic starch. Likewise, the plasticizer typically constitutes from about 2 wt. % to about 60 wt. %, in some embodiments from about 5 wt. % to about 50 wt. %, and in some embodiments, from about 10 wt. % to about 40 wt. % of the thermoplastic starch. The plasticizers may likewise constitute from about 0.1 wt. % to about 40 wt. %, in some embodiments from about 1 wt. % to about 35 wt. %, and in some embodiments, from about 5 to about 30 wt. % of the water-barrier layer. Further, starches may constitute from about 0.5 wt. % to about 45 wt. %, in some embodiments from about 5 wt. % to about 35 wt. %, and in some embodiments, from about 10 to about 30 wt. % of the film.

Batch and/or continuous melt blending techniques may be employed to blend the starch and plasticizer. For example, a mixer/kneader, Banbury mixer, Farrel continuous mixer, single-screw extruder, twin-screw extruder, roll mill, etc., may be utilized. One particularly suitable melt-blending device is a co-rotating, twin-screw extruder (e.g., USALAB twin-screw extruder available from Thermo Electron Corporation of Stone, England or an extruder available from Coperion Werner Pfreiderer from Ramsey, N.J.). Such extruders may include feeding and venting ports and provide high intensity distributive and dispersive mixing. For example, a starch polymer may be initially fed to a feeding port of the twin-screw extruder. Thereafter, a plasticizer may be injected into the starch composition. Alternatively, the starch may be simultaneously fed to the feed throat of the extruder or separately at a different point along its length. Melt blending may occur at any of a variety of temperatures, such as from about 30° C. to about 200° C., in some embodiments, from about 40° C. to about 160° C., and in some embodiments, from about 50° C. to about 150° C.

Of course, other additives may also be employed in the water-barrier layer. Dispersion aids, for instance, may be employed to help create a uniform dispersion of the aforementioned starch/plasticizer mixture and retard or prevent separation of the thermoplastic starch into constituent phases. Likewise, the dispersion aids may also improve the water dispersibility. When employed, the dispersion aid(s) typically constitute from about 0.01 wt. % to about 10 wt. %, in some embodiments from about 0.1 wt. % to about 5 wt. %, and in some embodiments, from about 0.5 wt. % to about 4 wt. % of the thermoplastic starch.

Although any dispersion aid may generally be employed in the present invention, surfactants having a certain hydrophilic/lipophilic balance ("HLB") may improve the long-term stability of the composition. The HLB index is well known in the art and is a scale that measures the balance between the hydrophilic and lipophilic solution tendencies of a compound. The HLB scale ranges from 1 to approximately 50, with the lower numbers representing highly lipophilic tendencies and the higher numbers representing highly hydrophilic tendencies. In some embodiments of the present invention, the HLB value of the surfactants is from about 1 to about 20, in some embodiments from about 1 to about 15 and in some embodiments, from about 2 to about 10. If desired, two or more surfactants may be employed that have HLB values either below or above the desired value, but together have an average HLB value within the desired range.

One particularly suitable class of surfactants for use in the present invention are nonionic surfactants, which typically have a hydrophobic base (e.g., long chain alkyl group or an alkylated aryl group) and a hydrophilic chain (e.g., chain containing ethoxy and/or propoxy moieties). For instance, some suitable nonionic surfactants that may be used include, but are not limited to, ethoxylated alkylphenols, ethoxylated and propoxylated fatty alcohols, polyethylene glycol ethers of methyl glucose, polyethylene glycol ethers of sorbitol, ethylene oxide-propylene oxide block copolymers, ethoxylated esters of fatty ($C_8$-$C_{18}$) acids, condensation products of ethylene oxide with long chain amines or amides, condensation products of ethylene oxide with alcohols, fatty acid esters, monoglyceride or diglycerides of long chain carboxylic acids, and mixtures thereof. In one particular embodiment, the nonionic surfactant may be a fatty acid ester, such as a sucrose fatty acid ester, glycerol fatty acid ester, propylene glycol fatty acid ester, sorbitan fatty acid ester, pentaerythritol fatty acid ester, sorbitol fatty acid ester, and so forth. The fatty acid used to form such esters may be saturated or unsaturated, substituted or unsubstituted, and may contain from 6 to 22 carbon atoms, in some embodiments from 8 to 18 carbon atoms, and in some embodiments, from 12 to 14 carbon atoms. In one particular embodiment, mono- and di-glycerides of fatty acids may be employed in the present invention.

In addition to the components noted above, still other additives may also be incorporated into the film of the present invention, such as melt stabilizers, processing stabilizers, heat stabilizers, light stabilizers, antioxidants, heat aging stabilizers, whitening agents, antiblocking agents, bonding agents, lubricants, fillers, etc.

II. Water-Dispersible Core Layer

The water-dispersible layer of the film will generally break apart into smaller pieces or completely dissolve when placed in an aqueous environment. The amount of time needed for dispersal of the water-dispersible layer will typically depend at least in part upon the particular end-use design criteria. Typically, the water-dispersible layer will be fully dispersed within the aqueous environment within about 60 minutes, suitably within about 15 minutes, more suitably within about 5 minutes, and most suitably within about 30 seconds.

A. Water-Soluble Polymer

To impart the desired degree of dispersibility, the water-dispersible layer includes at least one water-soluble polymer. The water-soluble polymer may be formed from monomers such as vinyl pyrrolidone, hydroxyethyl acrylate or methacrylate (e.g., 2-hydroxyethyl methacrylate), hydroxypropyl acrylate or methacrylate, acrylic or methacrylic acid, acrylic or methacrylic esters or vinyl pyridine, acrylamide, vinyl acetate, vinyl alcohol, ethylene oxide, derivatives thereof, and so forth. Other examples of suitable monomers are described in U.S. Pat. No. 4,499,154 to James, et al., which is incorporated herein in its entirety by reference thereto for all purposes. The resulting polymers may be homopolymers or interpolymers (e.g., copolymer, terpolymer, etc.), and may be nonionic, anionic, cationic, or amphoteric. In addition, the polymer may be of one type (i.e., homogeneous), or mixtures of different polymers may be used (i.e., heterogeneous). In one particular embodiment, the water-soluble polymer contains a repeating unit having a functional hydroxyl group, such as polyvinyl alcohol ("PVOH"), copolymers of polyvinyl alcohol (e.g., ethylene vinyl alcohol copolymers, methyl methacrylate vinyl alcohol copolymers, etc.), etc.

Vinyl alcohol polymers, for instance, have at least two or more vinyl alcohol units in the molecule and may be a homopolymer of vinyl alcohol, or a copolymer containing other monomer units. Vinyl alcohol homopolymers may be obtained by complete hydrolysis of a vinyl alkanoate polymer, such as vinyl formate, vinyl acetate, vinyl propionate, etc. Vinyl alcohol copolymers may be obtained by incomplete hydrolysis of a vinyl alkanoate with an olefin having 2 to 30 carbon atoms, such as ethylene, propylene, 1-butene, etc.; an unsaturated carboxylic acid having 3 to 30 carbon atoms, such as acrylic acid, methacrylic acid, crotonic acid, maleic acid, fumaric acid, etc., or an ester, salt, anhydride or amide thereof; an unsaturated nitrile having 3 to 30 carbon atoms, such as acrylonitrile, methacrylonitrile, etc.; a vinyl ether having 3 to 30 carbon atoms, such as methyl vinyl ether, ethyl vinyl ether, etc.; and so forth. The degree of hydrolysis may be selected to optimize solubility, etc., of the polymer. For example, the degree of hydrolysis may be from about 60 mole % to about 95 mole %, in some embodiments from about 80 mole % to about 90 mole %, and in some embodiments, from about 85 mole % to about 89 mole %. Examples of suitable partially hydrolyzed polyvinyl alcohol polymers are available under the designation CELVOL™ 203, 205, 502, 504, 508, 513, 518, 523, 530, or 540 from Celanese Corp. Other suitable partially hydrolyzed polyvinyl alcohol polymers are available under the designation ELVANOL™ 50-14, 50-26, 50-42, 51-03, 51-04, 51-05, 51-08, and 52-22 from DuPont.

B. Biodegradable Polymers

If desired, biodegradable polymers may also be employed in the water-dispersible layer to enhance its biodegradability under storage conditions. The biodegradable polymers may or may not be water soluble. For instance, suitable water-soluble biodegradable polymers may include the aforementioned chemically modified starch polymers (e.g., hydroxyalkyl starch). Likewise, biodegradable polymers that are not water soluble may include the aforementioned synthetic polyesters (e.g., aliphatic-aromatic copolyesters). Combinations of such polymers may also be employed. When employed, the biodegradable polymers typically constitute from about 50 wt. % to about 95 wt. %, in some embodiments from about 60 wt. % to about 90 wt. %, and in some embodiments, from about 70 wt. % to about 85 wt. % of the polymer content of the water-dispersible layer. Likewise, in such embodiments, water-soluble polymers typically constitute from about 5 wt. % to about 50 wt. %, in some embodiments from about 10 wt. % to about 40 wt. %, and in some embodiments, from about 15 wt. % to about 30 wt. % of the polymer content of the layer.

In one particular embodiment, for example, the water-dispersible layer contains a combination of water-soluble polymers (e.g., polyvinyl alcohol), starch polymers (e.g., chemically modified starch), and synthetic biodegradable polyesters (e.g., aliphatic-aromatic copolyester). In such embodiments, the starch polymers may constitute from about 30 wt. % to about 70 wt. %, in some embodiments from about 40 wt. % to about 60 wt. %, and in some embodiments, from about 45 wt. % to about 55 wt. % of the polymer content of the layer, and the synthetic biodegradable polyesters may constitute from about 10 wt. % to about 40 wt. %, in some embodiments from about 15 wt. % to about 35 wt. %, and in some embodiments, from about 20 wt. % to about 30 wt. % of the polymer content of the layer.

In another embodiment, for example, the water-dispersible layer contains a combination of water-soluble polymers (e.g., polyvinyl alcohol) and synthetic biodegradable polyesters (e.g., aliphatic-aromatic copolyester). In such embodiments, the water-soluble polymers may constitute from about 50 wt. % to about 95 wt. %, in some embodiments from about 60 wt. % to about 90 wt. %, and in some embodiments, from about 70 wt. % to about 85 wt. % of the polymer content of the layer, and the synthetic biodegradable polyesters may constitute from about 10 wt. % to about 50 wt. %, in some embodiments from about 10 wt. % to about 40 wt. %, and in some embodiments, from about 15 wt. % to about 30 wt. % of the polymer content of the layer.

C. Plasticizers

Plasticizers may also be employed in certain embodiments of the water-dispersible layer. Suitable plasticizers may include those described above, such as polyhydric alcohols. When employed, plasticizers typically constitute from about 5 wt. % to about 50 wt. %, in some embodiments from about 10 wt. % to about 40 wt. %, and in some embodiments, from about 15 wt. % to about 30 wt. % of the water-dispersible layer. In one particular embodiment, for example, the water-dispersible layer contains a combination of water-soluble polymers (e.g., polyvinyl alcohol) and a plasticizer. The water-soluble polymers may constitute from about 50 wt. % to about 95 wt. %, in some embodiments from about 60 wt. % to about 90 wt. %, and in some embodiments, from about 70 wt. % to about 85 wt. % of the water-dispersible layer, and the plasticizer may constitute from about 5 wt. % to about 50 wt. %, in some embodiments from about 10 wt. % to about 40 wt. %, and in some embodiments, from about 15 wt. % to about 30 wt. % of the polymer content of the layer.

D. Fillers

If desired, fillers may also be employed in the water-dispersible layer. Fillers are particulates or other forms of material that may be added to the film polymer extrusion blend and that will not chemically interfere with the extruded film, but which may be uniformly dispersed throughout the film. Fillers may serve a variety of purposes, including enhancing film opacity and/or breathability (i.e., vapor-permeable and substantially liquid-impermeable). For instance, filled films may be made breathable by stretching, which causes the polymer to break away from the filler and create microporous passageways. Breathable microporous elastic films are described, for example, in U.S. Pat. Nos. 5,997,981; 6,015,764; and 6,111,163 to McCormack, et al.; U.S. Pat. No. 5,932,497 to Morman, et al.; U.S. Pat. No. 6,461,457 to Taylor, et al., which are incorporated herein in their entirety by reference thereto for all purposes. Further, hindered phenols are commonly used as an antioxidant in the production of films. Some suitable hindered phenols include those available from Ciba Specialty Chemicals under the trade name "Irganox®", such as Irganox® 1076, 1010, or E 201. Moreover, bonding agents may also be added to the film to facilitate bonding of the film to additional materials (e.g., nonwoven webs). Examples of such bonding agents include hydrogenated hydrocarbon resins. Other suitable bonding agents are described in U.S. Pat. No. 4,789,699 to Kieffer et al. and U.S. Pat. No. 5,695,868 to McCormack, which are incorporated herein in their entirety by reference thereto for all purposes.

When employed, the filler may include particles having any desired size, such as those having an average size of from about 0.5 to about 10 micrometers, in some embodiments, from about 1 to about 8 micrometers, and in some embodiments, from about 2 to about 6 micrometers. Suitable particles for use as a filler may include inorganic oxides, such as calcium carbonate, kaolin clay, silica, alumina, barium carbonate, sodium carbonate, titanium dioxide, zeolites, magnesium carbonate, calcium oxide, magnesium oxide, aluminum hydroxide, talc, etc.; sulfates, such as barium sulfate, magnesium sulfate, aluminum sulfate, etc.; cellulose-type powders (e.g., pulp powder, wood powder, etc.); carbon; cyclodextrins; synthetic polymers (e.g., polystyrene), and so forth. Still other suitable particles are described in U.S. Pat. Nos. 6,015,764 and 6,111,163 to McCormack, et al.; U.S. Pat. No. 5,932,497 to Morman, et al.; U.S. Pat. No. 5,695,868 to McCormack; U.S. Pat. No. 5,855,999 to McCormack, et al.; U.S. Pat. No. 5,997,981 to McCormack et al.; and U.S. Pat. No. 6,461,457 to Taylor, et al., which are incorporated herein in their entirety by reference thereto for all purposes.

Although not required, the filler may optionally be coated with a modifier (e.g., fatty acid, such as stearic acid or behenic acid) to facilitate the free flow of the particles in bulk and their ease of dispersion into the composition. Further, the filler may also be coated with a liquid additive to reduce coupling at the resin-filler interface and facilitate debonding of filler from polymer matrix during stretching. This is especially useful for the polar biodegradable polymers, which demonstrate strong interaction with fillers. Examples of such additives include surfactants, such as silicone glycol copolymers available from Dow Corning Corporation. Other suitable additives for this purpose may include titanates available from Kenrich Petrochemicals, Inc. of Bayonne, N.J. under the designations Ken-React® LICA® 01, React® LICA® 12, Ken-React® CAPOW®, Ken-React® CAPS® and zirconates available from Kenrich under the designation Ken-React® CAPS NZ 01/L. The filler may be pre-compounded with such additives before mixing with the resin, or the additives may be compounded with the resin and fillers at the melt-blending step.

In one particular embodiment, for example, the water-dispersible layer contains a combination of water-soluble polymers and a filler. In such embodiments, the filler typically constitutes from about 1 wt. % to about 30 wt. %, in some embodiments from about 2 wt. % to about 25 wt. %, and in some embodiments, from about 5 wt. % to about 20 wt. % of the water-dispersible layer. Likewise, water-soluble polymers typically constitute from about 70 wt. % to about 99 wt. %, in some embodiments from about 75 wt. % to about 98 wt. %, and in some embodiments, from about 80 wt. % to about 95 wt. % of the water-dispersible layer.

E. Additional Additives

Besides the components noted above, still other additives may also be incorporated into the water-dispersible layer, such as melt stabilizers, processing stabilizers, heat stabilizers, light stabilizers, antioxidants, heat aging stabilizers, whitening agents, antiblocking agents, bonding agents, lubricants etc.

II. Film Construction

The film of the present invention contains a water-dispersible core layer that is positioned adjacent to a water-barrier skin layer. Of course, a variety of other layers may also be employed in the film as desired. In one embodiment, for example, it may be desirable to employ two skin layers that sandwich the core layer. If desired, both of the skin layers may be formed as a biodegradable water-barrier in the manner described herein. Alternatively, one skin layer may be formed from different components, such as traditional film-forming materials (e.g., polyolefin). Regardless of the number of layers, however, the water-dispersible core layer typically constitutes a substantial portion of the weight of the film, such as from about 50 wt. % to about 99 wt. %, in some embodiments from about 55 wt. % to about 90 wt. %, and in some embodiments, from about 60 wt. % to about 85 wt. % of the film. On the other hand, the skin layer(s) such as from about 1 wt. % to about 50 wt. %, in some embodiments from about 10 wt. % to about 45 wt. %, and in some embodiments, from about 15 wt. % to about 40 wt. % of the film.

Each skin layer may also have a thickness of from about 0.1 to about 10 micrometers, in some embodiments from about 0.5 to about 5 micrometers, and in some embodiments, from about 1 to about 2.5 micrometers. Likewise, the core layer may have a thickness of from about from about 1 to about 40 micrometers, in some embodiments from about 2 to about 25 micrometers, and in some embodiments, from about 5 to about 20 micrometers. The total thickness of the film may generally vary depending upon the desired use. Nevertheless, the film thickness is typically minimized to reduce the time needed for the film to disperse in water. Thus, in most embodiments of the present invention, the film has a total thickness of about 50 micrometers or less, in some embodiments from about 1 to about 40 micrometers, in some embodiments from about 2 to about 35 micrometers, and in some embodiments, from about 5 to about 30 micrometers.

Despite having such a small thickness and good sensitivity in water, the film of the present invention is nevertheless able to retain good dry mechanical properties during use. One parameter that is indicative of the relative dry strength of the film is the ultimate tensile strength, which is equal to the peak stress obtained in a stress-strain curve. Desirably, the film of the present invention exhibits an ultimate tensile strength in the machine direction ("MD") of from about 10 to about 80 Megapascals (MPa), in some embodiments from about 15 to about 60 MPa, and in some embodiments, from about 20 to about 50 MPa, and an ultimate tensile strength in the cross-machine direction ("CD") of from about 2 to about 40 Megapascals (MPa), in some embodiments from about 4 to about 40 MPa, and in some embodiments, from about 5 to about 30 MPa. Although possessing good strength, it is also desirable that the film is not too stiff. One parameter that is indicative of the relative stiffness of the film (when dry) is Young's modulus of elasticity, which is equal to the ratio of the tensile stress to the tensile strain and is determined from the slope of a stress-strain curve. For example, the film typically exhibits a Young's modulus in the machine direction ("MD") of from about 50 to about 1200 Megapascals ("MPa"), in some embodiments from about 100 to about 800 MPa, and in some embodiments, from about 150 to about 600 MPa, and a Young's modulus in the cross-machine direction ("CD") of from about 50 to about 1000 Megapascals ("MPa"), in some embodiments from about 100 to about 800 MPa, and in some embodiments, from about 150 to about 500 MPa. The MD elongation of the film may also be about 40% or more, in some embodiments about 60% or more, and in some embodiments, about 80% or more.

Other properties of the resulting film may generally vary as desired. For example, depending on the intended application, the film may be generally liquid and vapor-impermeable or generally liquid impermeable, yet vapor-permeable (i.e., "breathable"). Breathable films, for example, are often used in absorbent articles (e.g., outer cover) in which it is desired to allow moisture to escape from the absorbent core through the film. Breathable films may be formed with the use of a filler, such as described above. Filled films may be made breathable by stretching, which causes the polymer to break away from the filler and create microporous passageways. Techniques for forming microporous films are described, for example, in U.S. Pat. No. 7,153,569 to Kaufman, et al., as well as U.S. Application Publication Nos. 2005/0208294 to Kaufman, et al. and 2006/0149199 to Topolkaraev, et al., all of which are incorporated herein in their entirety by reference thereto for all purposes.

In embodiments in which it is desired to impart breathability, the film typically exhibits a water vapor transmission rate (WVTR) of about 800 grams/m$^2$-24 hours or more, in some embodiments about 1,000 grams/m$^2$-24 hours or more, in some embodiments about 1,200 grams/m$^2$-24 hours or more, and in some embodiments, from about 1,500 to about 10,000 grams/m$^2$-24 hours. The film may also limit the amount of liquid water that passes therethrough upon the application of pressure, i.e., it resists a hydrostatic pressure ("hydrohead") of about 50 millibar or more, in some embodiments about 70 millibar or more, in some embodiments about 80 millibar or more, and in some embodiments, about 100 millibar or more without allowing liquid water to pass.

The multi-layered film of the present invention may be prepared by co-extrusion of the layers, extrusion coating, or by any conventional layering process. Two particularly advantageous processes are cast film coextrusion processes and blown film coextrusion processes. In such processes, two or more of the film layers are formed simultaneously and exit the extruder in a multilayer form. Some examples of such processes are described in U.S. Pat. No. 6,075,179 to McCormack, et al. and U.S. Pat. No. 6,309,736 to McCormack, et al., which are incorporated herein in their entirety by reference thereto for all purposes. Processes for producing blown films are likewise described, for instance, in U.S. Pat. No. 3,354,506 to Raley; U.S. Pat. No. 3,650,649 to Schippers; and U.S. Pat. No. 3,801,429 to Schrenk et al., as well as U.S. Patent Application Publication Nos. 2005/0245162 to McCormack, et al. and 2003/0068951 to Boggs, et al., all of which are incorporated herein in their entirety by reference thereto for all purposes.

Referring to FIG. 1, for instance, one embodiment of a method for forming a co-extruded cast film is shown. In the particular embodiment of FIG. 1, the raw materials for the skin layer (not shown) are supplied to a first extruder 81 and the raw material for the core layer (not shown) are supplied to a second extruder 82. The extruders feed the compounded materials to a die 80 that casts the layers onto a casting roll 90 to form a two-layered precursor film 10a. The casting roll 90 may optionally be provided with embossing elements to impart a pattern to the film. Typically, the casting roll 90 is kept at temperature sufficient to solidify and quench the sheet 10a as it is formed, such as from about 20 to 60° C. If desired, a vacuum box may be positioned adjacent to the casting roll 90 to help keep the precursor film 10a close to the surface of the roll 90. Additionally, air knives or electrostatic pinners may help force the precursor film 10a against the surface of the casting roll 90 as it moves around a spinning roll. An air knife is a device known in the art that focuses a stream of air at a very high flow rate to pin the edges of the film.

Once cast, the film 10a may then be optionally oriented in one or more directions to further improve film uniformity and reduce thickness. Orientation may also form micropores in a film containing a filler, thus providing breathability to the film. For example, the film may be immediately reheated to a temperature below the melting point of one or more polymers in the film, but high enough to enable the composition to be drawn or stretched. In the case of sequential orientation, the "softened" film is drawn by rolls rotating at different speeds of rotation such that the sheet is stretched to the desired draw ratio in the longitudinal direction (machine direction). This "uniaxially" oriented film may then be laminated to a fibrous web. In addition, the uniaxially oriented film may also be oriented in the cross-machine direction to form a "biaxially oriented" film. For example, the film may be clamped at its lateral edges by chain clips and conveyed into a tenter oven. In the tenter oven, the film may be reheated and drawn in the cross-machine direction to the desired draw ratio by chain clips diverged in their forward travel.

Referring again to FIG. 1, for instance, one method for forming a uniaxially oriented film is shown. As illustrated, the precursor film 10a is directed to a film-orientation unit 100 or machine direction orienter ("MDO"), such as commercially available from Marshall and Willams, Co. of Providence, R.I. The MDO has a plurality of stretching rolls (such as from 5 to 8) which progressively stretch and thin the film in the machine direction, which is the direction of travel of the film through the process as shown in FIG. 1. While the MDO 100 is illustrated with eight rolls, it should be understood that the number of rolls may be higher or lower, depending on the level of stretch that is desired and the degrees of stretching between each roll. The film may be stretched in either single or multiple discrete stretching operations. It should be noted that some of the rolls in an MDO apparatus may not be operating at progressively higher speeds. If desired, some of the rolls of the MDO 100 may act as preheat rolls. If present, these first few rolls heat the film 10a above room temperature (e.g., to 125° F.). The progressively faster speeds of adjacent rolls in the MDO act to stretch the film 10a. The rate at which the stretch rolls rotate determines the amount of stretch in the film and final film weight.

The resulting film 10b may then be wound and stored on a take-up roll 60. While not shown here, various additional potential processing and/or finishing steps known in the art, such as slitting, treating, aperturing, printing graphics, or lamination of the film with other layers (e.g., nonwoven web materials), may be performed without departing from the spirit and scope of the invention.

III. Articles

The water-sensitive biodegradable film of the present invention may be used in a wide variety of applications. For example, as indicated above, the film may be used in an absorbent article. An "absorbent article" generally refers to any article capable of absorbing water or other fluids. Examples of some absorbent articles include, but are not limited to, personal care absorbent articles, such as diapers, training pants, absorbent underpants, incontinence articles, feminine hygiene products (e.g., sanitary napkins, pantiliners, etc.), swim wear, baby wipes, and so forth; medical absorbent articles, such as garments, fenestration materials, underpads, bedpads, bandages, absorbent drapes, and medical wipes; food service wipers; clothing articles; and so forth. Several examples of such absorbent articles are described in U.S. Pat. No. 5,649,916 to DiPalma, et al.; U.S. Pat. No. 6,110,158 to Kielpikowski; U.S. Pat. No. 6,663,611 to Blaney, et al., which are incorporated herein in their entirety by reference thereto for all purposes. Still other suitable articles are described in U.S. Patent Application Publication No. 2004/0060112 A1 to Fell et al., as well as U.S. Pat. No. 4,886,512 to Damico et al.; U.S. Pat. No. 5,558,659 to Sherrod et al.; U.S. Pat. No. 6,888,044 to Fell et al.; and U.S. Pat. No. 6,511,465 to Freiburger et al., all of which are incorporated herein in their entirety by reference thereto for all purposes. Materials and processes suitable for forming such absorbent articles are well known to those skilled in the art.

The films of the present invention are particularly useful as backsheets for disposable absorbent articles, and in particular for flushable interlabial pads. In such embodiments, the film is positioned so that the water-barrier skin layer faces the body of the user so that it can limit the rate of disintegration and degradation upon exposure to bodily fluids (e.g., urine, menses, etc.). Nevertheless, the presence of the water-dispersible core layer allows the film to be readily disintegrated after it is flushed.

Figure 2:
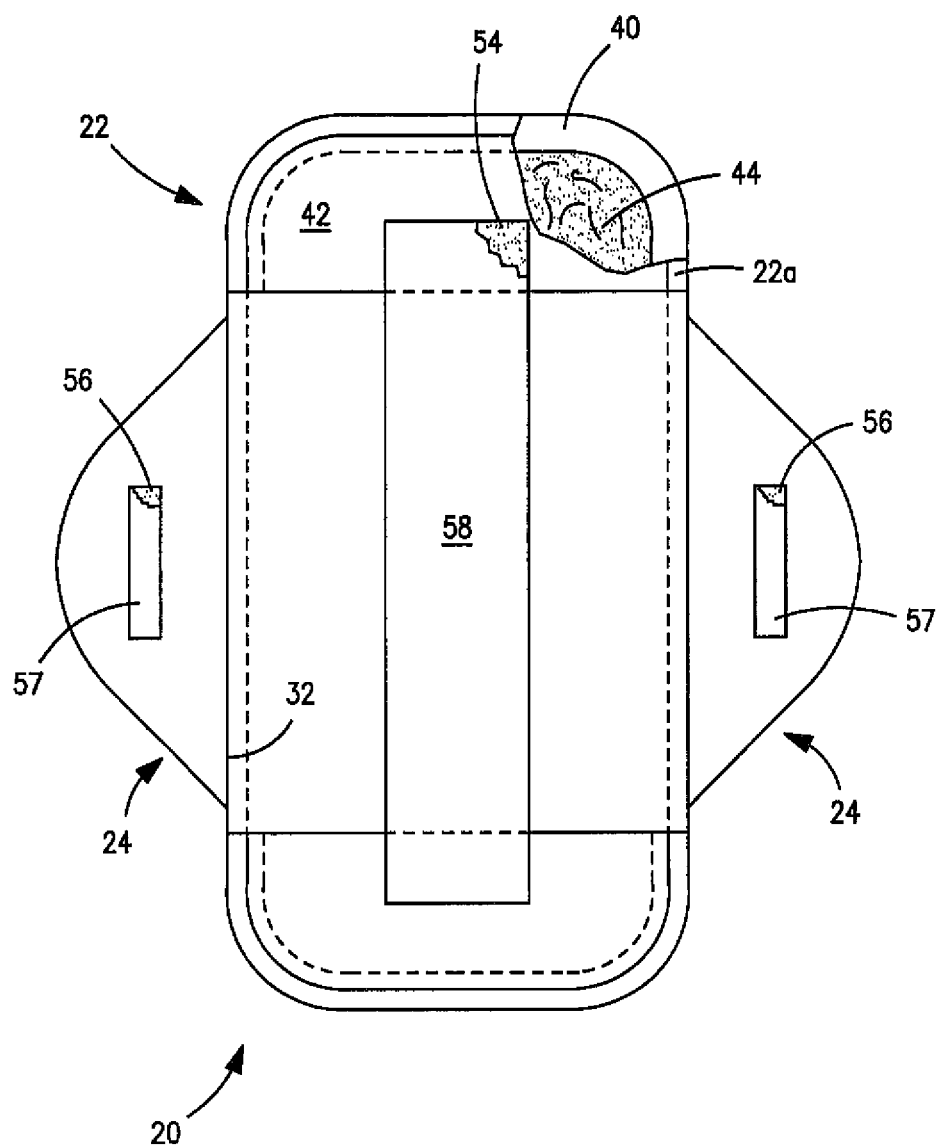
FIG. 2 is a top view of an absorbent article that may be formed in accordance with one embodiment of the present invention.

In this regard, one particular embodiment of a sanitary napkin that may employ the film of the present invention will now be described in more detail. For purposes of illustration only, an absorbent article 20 is shown in FIG. 2 as a sanitary napkin for feminine hygiene. In the illustrated embodiment, the absorbent article 20 includes a main body portion 22 containing a topsheet 40, an outer cover or backsheet 42, an absorbent core 44 positioned between the backsheet 42 and the topsheet 40, and a pair of flaps 24 extending from each longitudinal side 22a of the main body portion 22. The topsheet 40 defines a body-facing surface of the absorbent article 20. The absorbent core 44 is positioned inward from the outer periphery of the absorbent article 20 and includes a body-facing side positioned adjacent the topsheet 40 and a garment-facing surface positioned adjacent the backsheet 42.

The backsheet 42 is generally liquid-impermeable and designed to face the inner surface, i.e., the crotch portion of an undergarment (not shown). In one particular embodiment, the film of the present invention is used to form the backsheet 42 so that the water-barrier layer faces the body-facing surface and the water-dispersible layer faces the garment-facing surface. The backsheet 42 may permit a passage of air or vapor out of the absorbent article 20, while still blocking the passage of liquids.

The topsheet 40 is generally designed to contact the body of the user and is liquid-permeable. The topsheet 40 may surround the absorbent core 44 so that it completely encases the absorbent article 20. Alternatively, the topsheet 40 and the backsheet 42 may extend beyond the absorbent core 44 and be peripherally joined together, either entirely or partially, using known techniques. Typically, the topsheet 40 and the backsheet 42 are joined by adhesive bonding, ultrasonic bonding, or any other suitable joining method known in the art. The topsheet 40 is sanitary, clean in appearance, and somewhat opaque to hide bodily discharges collected in and absorbed by the absorbent core 44. The topsheet 40 further exhibits good strike-through and rewet characteristics permitting bodily discharges to rapidly penetrate through the topsheet 40 to the absorbent core 44, but not allow the body fluid to flow back through the topsheet 40 to the skin of the wearer. For example, some suitable materials that may be used for the topsheet 40 include nonwoven materials, perforated thermoplastic films, or combinations thereof. A nonwoven fabric made from polyester, polyethylene, polypropylene, bicomponent, nylon, rayon, or like fibers may be utilized. For instance, a white uniform spunbond material is particularly desirable because the color exhibits good masking properties to hide menses that has passed through it. U.S. Pat. No. 4,801,494 to Datta, et al. and U.S. Pat. No. 4,908,026 to Sukiennik, et al. teach various other cover materials that may be used in the present invention.

The topsheet 40 may also contain a plurality of apertures (not shown) formed therethrough to permit body fluid to pass more readily into the absorbent core 44. The apertures may be randomly or uniformly arranged throughout the topsheet 40, or they may be located only in the narrow longitudinal band or strip arranged along the longitudinal axis X-X of the absorbent article 20. The apertures permit rapid penetration of body fluid down into the absorbent core 44. The size, shape, diameter and number of apertures may be varied to suit one's particular needs.

The absorbent article 20 also contains an absorbent core 44 positioned between the topsheet 40 and the backsheet 42. The absorbent core 44 may be formed from a single absorbent member or a composite containing separate and distinct absorbent members. It should be understood, however, that any number of absorbent members may be utilized in the present invention. For example, in one embodiment, the absorbent core 44 may contain an intake member (not shown) positioned between the topsheet 40 and a transfer delay member (not shown). The intake member may be made of a material that is capable of rapidly transferring, in the z-direction, body fluid that is delivered to the topsheet 40. The intake member may generally have any shape and/or size desired. In one embodiment, the intake member has a rectangular shape, with a length equal to or less than the overall length of the absorbent article 20, and a width less than the width of the absorbent article 20. For example, a length of between about 150 mm to about 300 mm and a width of between about 10 mm to about 60 mm may be utilized.

Any of a variety of different materials may be used for the intake member to accomplish the above-mentioned functions. The material may be synthetic, cellulosic, or a combination of synthetic and cellulosic materials. For example, airlaid cellulosic tissues may be suitable for use in the intake member. The airlaid cellulosic tissue may have a basis weight ranging from about 10 grams per square meter (gsm) to about 300 gsm, and in some embodiments, between about 100 gsm to about 250 gsm. In one embodiment, the airlaid cellulosic tissue has a basis weight of about 200 gsm. The airlaid tissue may be formed from hardwood and/or softwood fibers. The airlaid tissue has a fine pore structure and provides an excellent wicking capacity, especially for menses.

If desired, a transfer delay member (not shown) may be positioned vertically below the intake member. The transfer delay member may contain a material that is less hydrophilic than the other absorbent members, and may generally be characterized as being substantially hydrophobic. For example, the transfer delay member may be a nonwoven fibrous web composed of a relatively hydrophobic material, such as polypropylene, polyethylene, polyester or the like, and also may be composed of a blend of such materials. One example of a material suitable for the transfer delay member is a spunbond web composed of polypropylene, multi-lobal fibers. Further examples of suitable transfer delay member materials include spunbond webs composed of polypropylene fibers, which may be round, tri-lobal or poly-lobal in cross-sectional shape and which may be hollow or solid in structure. Typically the webs are bonded, such as by thermal bonding, over about 3% to about 30% of the web area. Other examples of suitable materials that may be used for the transfer delay member are described in U.S. Pat. No. 4,798,603 to Meyer, et al. and U.S. Pat. No. 5,248,309 to Serbiak, et al., which are incorporated herein in their entirety by reference thereto for all purposes. To adjust the performance of the invention, the transfer delay member may also be treated with a selected amount of surfactant to increase its initial wettability.

The transfer delay member may generally have any size, such as a length of about 150 mm to about 300 mm. Typically, the length of the transfer delay member is approximately equal to the length of the absorbent article 20. The transfer delay member may also be equal in width to the intake member, but is typically wider. For example, the width of the transfer delay member may be from between about 50 mm to about 75 mm, and particularly about 48 mm. The transfer delay member typically has a basis weight less than that of the other absorbent members. For example, the basis weight of the transfer delay member is typically less than about 150 grams per square meter (gsm), and in some embodiments, between about 10 gsm to about 100 gsm. In one particular embodiment, the transfer delay member is formed from a spunbonded web having a basis weight of about 30 gsm.

Besides the above-mentioned members, the absorbent core 44 may also include a composite absorbent member (not shown), such as a coform material. In this instance, fluids may be wicked from the transfer delay member into the composite absorbent member. The composite absorbent member may be formed separately from the intake member and/or transfer delay member, or may be formed simultaneously therewith. In one embodiment, for example, the composite absorbent member may be formed on the transfer delay member or intake member, which acts a carrier during the coform process described above.

The absorbent article 20 also typically contains an adhesive for securing to an undergarment. An adhesive may be provided at any location of the absorbent article 20, such as on the lower surface of the backsheet 42. In this particular embodiment, the backsheet 42 carries a longitudinally central strip of garment adhesive 54 covered before use by a peelable release liner 58, which may optionally be formed from the film of the present invention. Each of the flaps 24 may also contain an adhesive 56 positioned adjacent to the distal edge 34 of the flap 24. A peelable release liner 57, which may also be formed in accordance with the present invention, may cover the adhesive 56 before use. Thus, when a user of the sanitary absorbent article 20 wishes to expose the adhesives 54 and 56 and secure the absorbent article 20 to the underside of an undergarment, the user simply peels away the liners 57 and 58 and disposed them in a water-based disposal system (e.g., in a toilet).

Of course, the film of the present invention may also be used in applications other than absorbent articles. For example, the film may be employed as an individual wrap, packaging pouch, or bag for the disposal of a variety of articles, such as food products, absorbent articles, etc. Various suitable pouch, wrap, or bag configurations for absorbent articles are disclosed, for instance, in U.S. Pat. No. 6,716,203 to Sorebo, et al. and U.S. Pat. No. 6,380,445 to Moder, et al., as well as U.S. Patent Application Publication No. 2003/0116462 to Sorebo, et al., all of which are incorporated herein in their entirety by reference thereto for all purposes.

The present invention may be better understood with reference to the following examples.

Test Methods

Tensile Properties:

The strip tensile strength values were determined in substantial accordance with ASTM Standard D-5034. A constant-rate-of-extension type of tensile tester was employed. The tensile testing system was a Sintech 1/D tensile tester, which is available from MTS Systems Corp. The tensile tester was equipped with TESTWORKS 4.08B software from MTS Systems Corp. to support the testing. An appropriate load cell was selected so that the tested value fell within the range of 10-90% of the full scale load. The film samples were initially cut into dog-bone shapes with a center width of 3.0 mm before testing. The samples were held between grips having a front and back face measuring 25.4 millimeters×76 millimeters. The grip faces were rubberized, and the longer dimension of the grip was perpendicular to the direction of pull. The grip pressure was pneumatically maintained at a pressure of 40 pounds per square inch. The tensile test was run using a gauge length of 18.0 millimeters and a break sensitivity of 40%. Five samples were tested by applying the test load along the machine-direction and five samples were tested by applying the test load along the cross direction. During the test, samples were stretched at a crosshead speed of abut 127 millimeters per minute until breakage occurred. The modulus, peak stress, peak strain (i.e., % strain at peak load), and elongation were measured.

Water Disintegration Test:

The rate of film disintegration in tap water was tested using the INDA/EDANA "Slosh Box Disintegration Test" (FG 522.2 Tier 2), which is described below.

Testing Parameters

The slosh box water transport simulator consists of a transparent plastic tank that is mounted on an oscillating platform with speed and holding time controller. The angle of incline produced by the cam system produces a water motion equivalent to 60 cm/s (2 ft/s), which is the minimum design standard for wastewater flow rate in an enclosed collection system. The rate of oscillation is controlled mechanically by the rotation of a cam and level system and should be measured periodically throughout the test. This cycle mimics the normal back-and-forth movement of wastewater as it flows through sewer pipe.

Materials and Apparatus

1. Clear plastic tank (inside dimensions: 18 in (45.75 cm) L×12 in (30.5 cm) W×6.5 in (16.5 cm) H. A drain is added to the tank to assist in emptying and cleaning the apparatus.

2. Cam system with a lift of 2.678 in (68 mm) runs with a motor and controller capable of speeds up to 50 rpm.

3. Perforated Plate Screens (304 stainless-steel plates with round holes and staggered pattern) details:

Hole size, hole center pattern gauge, % open area
25 mm 1", 1¼" Staggered 11SWG, 58%
12 mm ½", 11/16" Staggered 16SWG, 48%
6 mm ¼", 5/16" Staggered 16SWG, 58%
3 mm ⅛", 3/16' Staggered 20SWG, 40%
1.5 mm 1/16", 3/32" Staggered 20SWG, 41%

4. Drying oven capable of maintaining a temperature of 40±3° C. for thermoplastic materials and 103±3° C. for non-plastic materials.

5. Shower head (approximately 2-in or 5-cm diameter) and hose assembly with rubber fitting for water supply faucet/tap.

6. Aluminum weigh pan: 43-mm and 57-mm diameter.

7. Forceps.

8. Analytical balance capable of measuring weights at least 2-decimal places (4-decimal place balance is preferred for better accuracy). The dry weight of the samples (initial and final) are determined by placing them in a tared aluminum weigh pan and drying them in an oven at either 40±3° C. for thermoplastic test materials or 103±3° C. for non-plastic test materials. The samples are cooled in a desiccator prior to weighing to prevent post-drying atmospheric moisture uptake.

Test Initiation

Room temperature tap water (softened and/or non-softened) or raw wastewater (2000 mL) is placed in the plastic container/tank. The timer is set for 6 hours (or longer) and cycle speed is set for 26 rpm. The preweighed product is placed in the tank and observed as it undergoes the agitation period. For toilet tissue, add a number of sheets that range in weight from 1 to 3 g. All other products may be added whole with no more than 1 article per test. A minimum of 1 g of test product is recommended so that adequate loss measurements can be made. The time to first breakup and full dispersion are recorded in the laboratory notebook. For pre-moistened products it is recommended to flush them down the toilet and drainline apparatus prior to putting them into the slosh box apparatus or rinse them by some other means. Other prerinsing techniques should be described in the study records.

Test Termination

The test is terminated when the product reaches a dispersion point of no piece larger than 1 in (25 mm)×1 in (25 mm) square in size or at the designated destructive sampling points. At the designated destructive sampling points, remove the clear plastic tank from the oscillating platform. Pour the entire contents of the plastic tank through a nest of screens arranged from top to bottom in the following order: 25.40 mm, 12.70 mm, 6.35 mm, 3.18 mm, 1.59 mm (diameter opening). Make sure that the perforated plate screens are set with the smooth side up. With a showerhead spray nozzle held approximately 10-15 cm (4-6 in) above the sieve, gently rinse the material through the nested screens for two minutes at a flow rate of 4 L/min (1 gal/min) being careful not to force passage of the retained material through the next smaller screen. The flow rate can be assessed by measuring the time it takes to fill a 4 L beaker. The average of three flow rates should be 60±2 s. The procedure is similar to that used in the INDA/EDANA spray impact test method (WSP 80.3). After the two minutes of rinsing, remove the top screen and continue to rinse the next smaller screen, still nested, for two additional minutes. Again, be careful not to force passage of retained material to the next smaller screen. After rinsing is complete, remove the retained material from each of the screens using forceps and/or commercial paintbrushes. Transfer the content from each screen to a separate, labeled aluminum weigh pan. Place the pan in a drying oven overnight at 103±3° C. (or some other appropriate temperature depending on the thermostability of the test material). Continue this procedure at each designated sampling time until all the test products are sampled. Allow dried samples to cool down in a desiccator. After all the samples are dry, weigh the materials from each of the retained fractions and calculate the percentage of disintegration based on the initial starting weight of the test material.

Aerobic Biodisintegration Test:

Aerobic biodisintegration was tested using the INDA/EDANA test (FG 514.1 Tier 1), which is described below. This test method is used to assess the rate and extent of biological disintegration of a flushable product in aerobic environments. Results from this test are used to predict the disintegration of a product in municipal biological wastewater treatment, aerobic sludge digestion, aerobic onsite wastewater treatment and aerobic aquatic environments.

Test Initiation: Each test product is run in triplicate and there is typically a minimum of three (3) predetermined destructive sampling times (a total of nine samples). A control sample should also be included for each destructive sampling time (a total of 3 samples). Each flask contains 1 L of prescreened activated sludge (see field sampling section above) or prescreened raw wastewater and river water at a dilution of 1:3 (1 part wastewater to 2 parts river water) and the test product (typically one article or in the case of toilet tissue 1-3 g). The river water is only used to assess an untreated discharge condition. For this test the dilution ratio of raw wastewater to river water was chosen to correspond with that used for conducting Ecological Risk Assessments in Europe (EU, 1996). Each test product should be preweighed in triplicate on at least a 2-place analytical balance (4-place preferred) and these weights recorded in the laboratory notebook for final percent disintegration calculations. Products that are pre-moistened (e.g., wet wipes) should be pre-rinsed prior to use. A dry weight correction should be made by measuring the average percent solids of five products (i.e., weight of pre-rinsed and dried sample divided by moist sample) and multiplying the wet weight by that amount. Additional flasks, (at least one for each product), are also prepared. They contain the same amount of the test product, but in 1 L of tap water. While these samples are not used in the weight loss calculations, results from these flasks are used to assess how much of the disintegration is due to the physical forces or hydrolysis as opposed to biological activity. Observations are made throughout the test and these flasks are sampled at the same time as the activated sludge (or raw wastewater/river water) samples.

Control flasks with the reference material are also evaluated at the three (3) sampling times. Each flask contains 1 L of prescreened activated sludge (or raw wastewater and river water) and one tampon or an appropriate alternative reference material). The control product should be preweighed on a 2-place analytical balance (or preferable a 4-place) and these weights recorded in the laboratory notebook for final percent disintegration calculations.

Following the presieving, 1 L of activated sludge (or raw wastewater and river water) is transferred to each flask and then placed on the rotary shaker. Next, the test product is added to the flasks. The rotary shaker is then turned on and set at a rate of 150 rpm. Visual observations of the test product in the tap water control should be recorded after 1 hour, 3 hour, and then daily during the first week. Periodically during the incubation period the solids that swirl up on the side of the flasks should be rinsed off with tap water in a wash bottle. This will also replenish any water that has been lost due to evaporation during the course of the test. The recommended sampling times for most products are at days 7, 14 and 28. If longer times are run, the activated sludge in the flasks should be replaced every 28 days. This test is conducted at room temperature (22±3° C.).

Test Termination: At the designated sampling times, a flask from each set of products being tested and the control sample is removed from the shaker table. Depending on the number of replicates, the tap water flask is also sampled at this time. At each sampling point the contents of a single flask are passed through a 1-mm size sieve. (A 1-mm size sieve is used to ensure that the product would no longer be visible in the environment). With a hand-held shower head spray nozzle held approximately 10-15 cm (4-6 in) above the sieve, gently rinsed for 2 min at a flow rate of 4 L/min (1 gal/min) to remove any activated sludge from the product residual. The flow rate can be assessed by measuring the time it takes to fill a 4 L beaker. The average of three flow rates (time in seconds) should be 60±2 s. This procedure is similar to that used in the INDA/EDANA spray impact test method (WSP 80.3). After rinsing, the retained material from the screen is removed with the aid of forceps and then transferred to a labeled aluminum weigh pan. Note in the study records if there appears to be an association of the activated sludge solids with the test product, which could cause a greater weight for the materials retained on the sieves. The pan is placed in the oven at 103±3° C. overnight (or some other appropriate temperature and time depending on the thermostability properties of the material; record temperature and holding time). After drying and cooling under desiccation, the sample is reweighed. This procedure is repeated at each designated sampling time until all the test products and controls are sampled. After all the samples are dried and weighed, the percentage of disintegration based on the initial starting weight of the test materials (samples and control) is recorded in the laboratory notebook.

Calculation: The percentage of product disintegration can be calculated using the following equation:

%Mass Loss=[1−dried weight of retained fraction on sieve(g)/initial dried weight of sample(g)]×100

The percent mass loss should be determined for each sample and the results recorded as the average for each sample time.

Anaerobic Biodegradation Test:

Anerobic biodegradation was tested using the INDA/EDANA test (FG 514.2 Tier 1), which is described below. In this method the test material is typically exposed to biologically active anaerobic digester sludge at 35±3° C. over a 28-day period, but other time periods may be used depending on the properties of the test material (e.g., 56 d) and other exposure media when appropriate (e.g., river sediment when assessing untreated discharge conditions). The disintegration of the test material is measured by weight and/or tensile strength loss over time. The conditions of this test are optimized for temperature and solids concentration to maximize the rate at which the test material will biologically disintegrate. Results from the anaerobic sludge test are used to assess the biological disintegration of a product in the sludge layer of a septic tank or in an anaerobic digester at a municipal wastewater treatment plant. These results can also be extrapolated to anaerobic surface water sediment environments or the test can be run with river sediment if a more realistic simulation is desired for untreated wastewater discharge conditions.

Test Initiation:

1. Sieve the anaerobic sludge (or river sediment if used to assess untreated wastewater discharge conditions) through a No. 18 mesh size screen (1 mm opening) to remove any solids greater than 1 mm in size. If an automated separator (e.g., Sweco™ Separator) is used for screening, then two screening decks with the coarser screen on top is recommended. This coarser screen helps keep the 1-mm screen from blinding. If river sediment is used, a 1:1 sediment/river water slurry may be needed to pass the solids through the sieve.

2. Pour the screened anaerobic sludge (or river sediment if used to assess untreated wastewater discharge conditions)) into a plastic mixing barrel (volume large enough for conducting the test) and cover with a plastic bag or other type of lid.

3. Insert the tubing from the nitrogen gas cylinder through a small hole in the bag or lid and secure it to the barrel with a clamp or duct tape in a position above the anaerobic sludge (or river sediment) to generate a gas blanket.

4. Turn the nitrogen gas on at a low flow rate so that it blankets the surface of the sludge (or sediment) in the barrel. This helps keep the sludge (or sediment) anaerobic during the transfer process.

5. Insert the stirrer blade and shaft through another small opening in the bag and lower the stirrer down to near the bottom of the barrel. When the nitrogen gas has had several minutes to fill the headspace in the barrel, turn the mixer on.

6. Use a peristaltic pump to transfer 1.5 L of anaerobic sludge (or river sediment if used to assess untreated wastewater discharge conditions)) into 2-L prelabeled reactor bottles (at least three bottles for each time point for statistical analysis purposes). Place a one-hole butyl rubber stopper on each bottle after it is filled.

7. Products that are pre-moistened (e.g., wet wipes) should be pre-rinsed prior to use. A dry weight correction should be made by measuring the average percent solids of five products (i.e., weight of pre-rinsed and dried sample divided by moist sample) and multiplying the wet weight by that amount. Add pre-weighed sample or reference material to each of the sample bottles, recap with butyl rubber stopper and gently invert each bottle (typically 2-3 times) to get the sample into the sludge (or sediment). It is recommended that 1-3 g of product be added (a minimum of 1 g) so that an accurate weight loss can be determined and that triplicate samples be prepared for each sampling time. Any other sample preparation (e.g., drying, rinsing, folding) or number of replicates should be documented in the study record.

8. Place the bottles in an incubator set at 35±3° C.

Test Termination On sampling days (typically days 7, 14, and 28), the content of each bottle is poured through a 1-mm size sieve. A 1-mm size sieve is used to ensure that the product would no longer be visible in the environment. Rinse the remaining sludge (or sediment) solids through the sieve with the tap water shower spray held approximately 10-15 cm (4-6 in) above the screen for 2 minutes at a flow rate of 4 L/min (1 gal/min). The flow rate can be assessed by measuring the time it takes to fill a 4 L beaker. The average of three flow rates (time in seconds) should be 60±2 s. This procedure is similar to that used in the INDA/EDANA spray impact test method (WSP 80.3). After rinsing, the retained material from the screen is removed with the aid of forceps and then transferred to a labeled aluminum weigh pan. Note in the study records if there appears to be an association of the anaerobic sludge solids (or sediment solids if assessing untreated discharge conditions) with the test product, which could cause a greater weight for the materials retained on the sieves. The pan is placed in the oven overnight at 103±3° C. (or some other appropriate temperature and time depending on the thermostability properties of the test material). After drying and cooling under desiccation, the sample is reweighed. This procedure is repeated at each designated sampling time until all of the test products and control are sampled. After all of the samples are dried and weighed, the percentage of disintegration based on the initial starting weight of the test materials (samples and control) is recorded in the laboratory notebook.

Calculation: The percentage of product disintegration can be calculated using the following equation:

%Mass Loss=[1−dried weight of retained fraction on sieve(g)/initial dried weight of sample(g)]×100

The percent mass loss should be determined for each sample and the results recorded as the average for each sample time.

EXAMPLE 1

A thermoplastic hydroxypropylated starch was formed as follows. Initially, a mixture of a hydroxypropylated starch (Glucosol 800, manufactured by Chemstar Products Company, Minneapolis, Minn.), surfactant (Excel P-40S, Kao Corporation, Tokyo, Japan), and plasticizer (sorbitol) was made at a ratio of the 66 parts of starch, 4 parts of surfactant, and 30 parts of plasticizer. Glucosol 800 has a weight average molecular weight of 2,900,000 grams per mole (determine by gel permeation chromatography) and a polydispersity index of about 28.

A Hobart mixer was used for mixing. The mixture was then added to a K-Tron feeder (K-Tron America, Pitman, N.J.) that fed the material into a co-rotating, twin-screw extruder (ZSK-30, diameter of 30 mm) that was manufactured by Werner and Pfleiderer Corporation of Ramsey, N.J. The screw length was 1328 millimeters. The extruder had 14 barrels, numbered consecutively 1-14 from the feed hopper to the die. The first barrel #1 received the mixture at 19 lbs/hr when the extruder was heated to a temperature for zones 1 to 7 of 100° C., 110° C., 124° C., 124° C., 124° C., 110° C., and 105° C., respectively. The screw speed was set at 160 rpm to achieve a melt pressure of 400-500 psi and a torque of 50-60%. In some cases, a vent was also opened to release steam generated due to the presence of the added water in the plasticizer and inherent moisture in the starch. The strands cooled down through a cooling belt (Minarik Electric Company, Glendale, Calif.). A pelletizer (Conair, Bay City, Mich.) was used to cut the strands to produce thermoplastic starch pellets, which were then collected and sealed in a bag.

EXAMPLE 2

A thermoplastic plasticized polyvinyl alcohol ("PVA") was formed as follows. Initially, a mixture of a polyvinyl alcohol (Elvanol 51-05, a granular polymer having a degree of hydrolysis of 87.0-89.0 mole % and manufactured by DuPont) and plasticizer (sorbitol) was made at a ratio of the 80 parts polyvinyl alcohol and 20 parts of plasticizer. A Hobart mixer was used for mixing. The mixture was then added to a K-Tron feeder (K-Tron America, Pitman, N.J.) that fed the material into a ZSK-30 co-rotating, twin-screw extruder as described above. The first barrel #1 received the mixture at 25 lbs/hr when the extruder was heated to a temperature for zones 1 to 7 of 150° C., 160° C., 185° C., 190° C., 190° C., 170° C., and 110° C., respectively. The screw speed was set at 160 rpm to achieve a melt pressure of 280-300 psi and a torque of 34-40%. In some cases, a vent was also opened release steam generated due to the presence of the added water in the plasticizer and inherent moisture in the starch. The strands cooled down through a cooling belt (Minarik Electric Company, Glendale, Calif.), A pelletizer (Conair, Bay City, Mich.) was used to cut the strands to produce polyvinyl alcohol pellets, which were then collected and sealed in a bag.

EXAMPLE 3

A plasticized polyvinyl alcohol was formed as follows. Initially, a mixture of a polyvinyl alcohol (Celvol 203, a polymer having a degree of hydrolysis of 87.0-89.0 mole % and manufactured by Celanese Chemicals) and plasticizer (sorbitol) was made at a ratio of the 80 parts polyvinyl alcohol and 20 parts of plasticizer. A Hobart mixer was used for mixing. The mixture was then added to a K-Tron feeder (K-Tron America, Pitman, N.J.) that fed the material into a ZSK-30 co-rotating, twin-screw extruder as described above. The first barrel #1 received the mixture at 25 lbs/hr when the extruder was heated to a temperature for zones 1 to 7 of 150° C., 160° C., 185° C., 190° C., 190° C., 170° C., and 110° C., respectively. The screw speed was set at 160 rpm to achieve a melt pressure of 280-300 psi and a torque of 34-40%. In some cases, a vent was also opened release steam generated due to the presence of the added water in the plasticizer and inherent moisture in the starch. The strands cooled down through a cooling belt (Minarik Electric Company, Glendale, Calif.). A pelletizer (Conair, Bay City, Mich.) was used to cut the strands to produce polyvinyl alcohol pellets, which were then collected and sealed in a bag.

EXAMPLE 4

A blend of hydroxypropylated starch and polyvinyl alcohol was formed as follows. Initially, a mixture of a hydroxypropylated starch (Glucosol 800), surfactant (Excel P-40S), plasticizer (sorbitol), and polyvinyl alcohol (Elvanol 51-05) was made at a ratio of the 36 parts of hydroxypropylated starch, 30 parts polyvinyl alcohol, 4 parts of surfactant, and 30 parts of plasticizer. A Hobart mixer was used for mixing. The mixture was then added to a K-Tron feeder (K-Tron America, Pitman, N.J.) that fed the material into a ZSK-30 co-rotating, twin-screw extruder as described above. The first barrel #1 received the mixture at 20 lbs/hr when the extruder was heated to a temperature for zones 1 to 7 of 95° C., 125° C., 140° C., 150° C., 150° C., 145° C., and 130° C., respectively. The screw speed was set at 150-160 rpm to achieve a melt pressure of 530-550 psi and a torque of 80-90%. In some cases, a vent was also opened release steam generated due to the presence of the added water in the plasticizer and inherent moisture in the starch. The strands cooled down through a cooling belt (Minarik Electric Company, Glendale, Calif.). A pelletizer (Corsair, Bay City, Mich.) was used to cut the strands to produce pellets, which were then collected and sealed in a bag.

EXAMPLE 5

A blend of starch and polyvinyl alcohol was formed as follows. Initially, a mixture of native corn starch (Cargill, Minneapolis, Minn.), surfactant (Excel P-40S), plasticizer (sorbitol), and polyvinyl alcohol (Elvanol 51-05) was made at a ratio of the 38 parts of starch, 30 parts polyvinyl alcohol, 2 parts of surfactant, and 30 parts of plasticizer. A Hobart mixer was used for mixing. The mixture was then added to a K-Tron feeder (K-Tron America, Pitman, N.J.) that fed the material into a ZSK-30 co-rotating, twin-screw extruder as described above. The first barrel #1 received the mixture at 20 lbs/hr when the extruder was heated to a temperature for zones 1 to 7 of 95° C., 125° C., 140° C., 150° C., 150° C., 145° C., and 130° C., respectively. The screw speed was set at 150-160 rpm to achieve a melt pressure of 530-550 psi and a torque of 80-90%. In some cases, a vent was also opened release steam generated due to the presence of the added water in the plasticizer and inherent moisture in the starch. The strands cooled down through a cooling belt (Minarik Electric Company, Glendale, Calif.). A pelletizer (Conair, Bay City, Mich.) was used to cut the strands to produce pellets, which were then collected and sealed in a bag.

EXAMPLE 6

A blend of hydroxypropylated starch and polyvinyl alcohol was formed as follows. Initially, a mixture of a hydroxypropylated starch (Glucosol 800), surfactant (Excel P-40S), plasticizer (sorbitol), and polyvinyl alcohol (Celvol 203) was made at a ratio of the 36 parts of starch, 30 parts polyvinyl alcohol, 4 parts of surfactant, and 30 parts of plasticizer. A Hobart mixer was used for mixing. The mixture was then added to a K-Tron feeder (K-Tron America, Pitman, N.J.) that fed the material into a ZSK-30 co-rotating, twin-screw extruder as described above. The first barrel #1 received the mixture at 10 lbs/hr when the extruder was heated to a temperature for zones 1 to 7 of 95° C., 125° C., 140° C., 150° C., 150° C., 145° C., and 130° C., respectively. The screw speed was set at 150-160 rpm to achieve a melt pressure of 530-550 psi and a torque of 80-90%. In some cases, a vent was also opened release steam generated due to the presence of the added water in the plasticizer and inherent moisture in the starch. The strands cooled down through a cooling belt (Minarik Electric Company, Glendale, Calif.). A pelletizer (Conair, Bay City, Mich.) was used to cut the strands to produce pellets, which were then collected and sealed in a bag.

EXAMPLES 7-9

Various combinations of the thermoplastic modified starch of Example 1 and the polyvinyl alcohol of Examples 2-3 were compounded with an Ecoflex® F BX 7011 resin (BASF, Florham Park, N.J.) using the ZSK-30 twin screw extruder described above. The strands from the die was pelletized. The extrusion conditions are set forth below in Tables 1-2:

TABLE 1

| | | Composition of Pellets | | |
|---|---|---|---|---|
| Example | Resin Feeding Rate (lb/hr) | Thermoplastic Modified Starch of Ex. 1 (wt. %) | Thermoplastic PVA of Ex. 2 (wt. %) | Ecoflex ® (wt. %) |
| 7 | 20 | 60 | 30 | 10 |
| 8 | 20 | 70 | 20 | 10 |
| 9 | 20 | 70 | 30 | 0 |

TABLE 2

| | | Extrusion Conditions | | | | | | | | | |
|---|---|---|---|---|---|---|---|---|---|---|---|
| Example | Extruder Speed (rpm) | Extruder Temperature Profile (° C.) | | | | | | | | $P_{melt}$ (psi) | Torque (%) |
| | | $T_1$ | $T_2$ | $T_3$ | $T_4$ | $T_5$ | $T_6$ | $T_7$ | $T_{melt}$ | | |
| 7 | 160 | 100 | 140 | 160 | 160 | 160 | 155 | 140 | 155 | 250-300 | 65-75 |
| 8 | 160 | 100 | 140 | 160 | 160 | 160 | 155 | 140 | 155 | 250-300 | 65-75 |
| 9 | 160 | 100 | 140 | 160 | 160 | 160 | 155 | 140 | 155 | 250-300 | 65-75 |

EXAMPLES 10-12

Glucosol 800 starch, Elvanol 51-05, sorbitol, and surfactant (Excel P-40S) were initially mixed in a Hobart mixer at 36%, 30%, 30%, and 4%, respectively.

The mixture was fed into ZSK-30 using K-Tron feeder. Separately, Ecoflex® F BX 7011 resin (BASF, Florham Park, N.J.) was fed from another K-Tron feeder into ZSK-30 for single-step compounding. This process reduces the thermal degradation of materials during blend preparation. The strands from the die were pelletized. The extrusion conditions are set forth below in Table 3 and 4.

TABLE 3

| | | Composition of Pellets | |
|---|---|---|---|
| Example | Resin Feeding Rate (lb/hr) | Mixture of Glucosol 800, Elvanol 51-05, sorbitol, and Excel P-40S (wt. %) | Ecoflex ® (wt. %) |
| 10 | 20 | 90 | 10 |
| 11 | 20 | 80 | 20 |
| 12 | 20 | 70 | 30 |

TABLE 4

Extrusion Conditions

| Example | Extruder Speed (rpm) | $T_1$ | $T_2$ | $T_3$ | Extruder Temperature Profile (° C.) $T_4$ | $T_5$ | $T_6$ | $T_7$ | $T_{melt}$ | $P_{melt}$ (psi) | Torque (%) |
|---|---|---|---|---|---|---|---|---|---|---|---|
| 10 | 160 | 100 | 124 | 150 | 150 | 150 | 145 | 130 | 144 | 290-310 | 80-90 |
| 11 | 160 | 100 | 124 | 150 | 150 | 150 | 145 | 130 | 144 | 290-310 | 80-90 |
| 12 | 160 | 100 | 124 | 150 | 150 | 150 | 145 | 130 | 144 | 290-310 | 80-90 |

EXAMPLES 13-15

Thermoplastic hydroxypropylated starch ("TPS") from Example 1, thermoplastic plasticized polyvinyl alcohol (Aqua-Sol™ 116, which is available from A. Schulman, Inc.), and Ecoflex® F BX 7011 resin (BASF, Florham Park, N.J.) were compounded at varying ratios using the ZSK-30 twin screw extruder described above. The strands from the die were pelletized. The extrusion conditions are set forth below in Table 5.

Screw Extruder (manufactured by Werner & Pfleiderer, Ramsey, N.J.) at a ratio of 60 wt. % Ecoflex and 40 wt. % TPS at throughput of 20 lbs/hr. The process temperatures were 140° C., 150° C., 155° C., 155° C., 155° C., 150° C., and 140° C. for Zones 1 to 7 on the extruder. The screw speed was 150 rpm. The melt temperature was 160° C. The strands were cooled on a fan-cooled conveyer belt and then pelletized.

The preparation of other blends containing different ratio of Ecoflex® F BX 7011 to TPS was similar to this process conditions. The range of TPS in the blends ranges from about 10% to 60% by weight.

TABLE 5

Extrusion Conditions

| Sample No. | Resin Feeding Rate (lb/hr) | TPS (%) | Aquasol (%) | Ecoflex (%) | Extruder Speed (rpm) | $T_1$ | $T_2$ | $T_3$ | Extruder Temperature Profile (° C.) $T_4$ | $T_6$ | $T_6$ | $T_7$ | $T_{melt}$ | $P_{melt}$ (psi) | Torque (%) |
|---|---|---|---|---|---|---|---|---|---|---|---|---|---|---|---|
| Example 13 | 30 | 70 | 30 | 0 | 160 | 100 | 135 | 170 | 170 | 165 | 150 | 150 | 162 | 250-300 | 70-79 |
| Example 14 | 30 | 90 | 30 | 10 | 160 | 100 | 135 | 170 | 170 | 165 | 150 | 150 | 162 | 250-300 | 70-79 |
| Example 15 | 30 | 70 | 20 | 10 | 150 | 100 | 135 | 170 | 170 | 165 | 150 | 150 | 162 | 250-300 | 70-79 |

EXAMPLE 16

A thermoplastic corn starch ("Corn TPS") was formed as follows. Initially, a mixture of corn starch and surfactant (Excel P-40S, Kao Corporation, Tokyo, Japan) was made in a kitchen mixer at a ratio of the 99 parts of potato starch to the 1 part of surfactant. The mixture was added to a gravimetric feeder (K-Tron America, Pitman, N.J., Model KCM-2) that fed the material into a Prism USALAB 16 Twin Screw Extruder (Thermo Electron Corp., Stone, England) at 2 pounds per hour. A plasticizer (mixture of 20 wt. % water and 80 wt. % glycerol) was pumped into zone 1. The pumping rate for the plasticizer was determined using a timer and was adjusted to achieve the desired ratio of the plasticizer to starch in the final composition. A vent was also provided at zone 9 to release steam generated due to the presence of the added water in the plasticizer and inherent moisture in the starch. The temperature profile for zones 1 to 10 was 50° C., 80° C., 100° C., 140° C., 140° C., 140° C., 120° C., 100° C., 80° C., and 60° C., respectively. The screw speed was set at 170 rpm so that the torque fluctuated between 60-75% during the processing. The extruded corn TPS strand contained 70 wt. % starch (a mixture of 99 wt. % potato starch and 1 wt. % Excel P-40S) and 30 wt. % plasticizer. The strand cooled down through a cooling belt (Bondine Electric Co., Chicago, Ill.). A pelletizer (Emerson Industrial Controls, Grand Island, N.Y.) was used to cut the strand to produce thermoplastic starch pellets.

EXAMPLE 17

To make blends, the Corn TPS of Example 16 was compounded with Ecoflex® F BX 7011 resin on a ZSK-30 Twin

EXAMPLE 18

A two-layered, co-extruded film was formed by the method of Example 11 (water-dispersible core layer) and the blend made by the method of Example 17 (water-barrier skin layer). More particularly, the water-barrier skin layer contained 70 wt. % Ecoflex® F BX 7011 resin, 9 wt. % sorbitol, and 21 wt. % corn starch, and the water-dispersible core layer contained 16 wt. % polyvinyl alcohol (Elvanol 51-05), 41 wt. % hydroxypropylated starch (Glucosol 800), 1.5 wt. % surfactant (Excel P-40S), 21 wt. % plasticizer (sorbitol), and 20.5 wt. % Ecoflex® F BX 7011 resin. The target weight of the layers was 16 wt. % of the film for the skin layer and 84 wt. % of the film for the core layer. The extrusion equipment was made by Randcastle (Little Falls, N.J.) and included two vertically mounted extruders that formed the two layers of the co-extruded film. The extruder for the core layer had a 0.75-inch diameter screw and the extruder for the skin layer had a 0.625-inch diameter. The extrudates were combined via feedblocks. The three (3) zones and feedblock of the skin extruder was set at temperatures of 320° F., 340° F., 340° F., and 350° F., respectively, and the three (3) zones and feedblock of the core extruder was set at 320° F., 330° F., 340° F., and 350° F., respectively. The die width was 10 inches.

The resulting cast film was collected at a speed of 15.6 feet per minute. The film had a total thickness of about 25.4 micrometers.

EXAMPLE 19

A two-layered, co-extruded film was formed as described in Example 18, except that the three (3) zones and feedblock of the skin extruder was set at temperatures of 330° F., 330° F., 350° F., and 350° F., respectively, and the three (3) zones and feedblock of the core extruder was set at 330° F., 340° F., 350° F., and 350° F., respectively. The melt temperature was 358° F.

EXAMPLE 20

A two-layered, co-extruded film was formed as described in Example 18, except that the water-dispersible core layer also contained 8 wt. % of filler (50 wt. % talc and 50 wt. % calcium carbonate). The two-layered film was collected and contained the skin layer in an amount of about 20 wt. % of the film.

EXAMPLE 21

A two-layered, co-extruded film was formed as described in Example 18, except that the water-dispersible core layer also contained 3 wt. % talc. Further, the three (3) zones and feedblock of the skin extruder was set at temperatures of 330° F., 330° F., 351° F., and 350° F., respectively, and the three (3) zones and feedblock of the core extruder was set at 330° F., 340° F., 350° F., and 350° F., respectively.

EXAMPLE 22

A two-layered, co-extruded film was formed as described in Example 18, except that the core layer contained 72 wt. % polyvinyl alcohol (Elvanol 51-05), 18 wt. % sorbitol, and 10 wt. % of an Entira™ Strong polymeric additive (DuPont). The target weight of the layers was 30 wt. % of the film for the skin layer and 70 wt. % of the film for the core layer.

Once formed, the films of Examples 19-22 were subjected to the above-described tensile tests. The estimated weight percentage of the layers was determined by optical microscopy. The results are set forth below in Table 6.

TABLE 6

| Average Mechanical Properties of the Film Samples | | | | | | | | | | |
|---|---|---|---|---|---|---|---|---|---|---|
| | Weight % | | Thickness (mil) | | Peak Stress (Mpa) | | Strain at Break (%) | | Modulus (Mpa) | |
| Example | Skin | Core | MD | CD | MD | CD | MD | CD | MD | CD |
| 19 | 16 | 84 | 1.02 | 0.99 | 26 | 15 | 81 | 5 | 487 | 342 |
| 20 | 16 | 84 | 0.96 | 1.02 | 27 | 20 | 66 | 7 | 599 | 489 |
| 21 | 16 | 84 | 0.86 | 0.91 | 24 | 17 | 68 | 23 | 476 | 388 |
| 22 | 30 | 70 | 0.66 | 0.81 | 34 | 10 | 130 | 34 | 193 | 158 |

EXAMPLE 23

A two-layered, co-extruded film was formed made by the method of Example 18. The preparation of water-dispersible core layer was described in Example 15. More particularly, the water-barrier skin layer contained 100 wt. % Ecoflex® F BX 7011 resin, and the water-dispersible core layer contained 20 wt. % thermoplastic plasticized polyvinyl alcohol (Aquasol), 70 wt. % hydroxpropylated starch (Glucosol 800), and 10 wt. % Ecoflex® F BX 7011 resin. The target weight of the layers was 16 wt. % of the film for the skin layer and 84 wt. % of the film for the core layer. The extrusion equipment was the same as employed in Example 16. The three (3) zones and feedblock of the skin extruder was set at temperatures of 320° F., 320° F., 320° F., and 320° F., respectively, and the three (3) zones and feedblock of the core extruder was set at 320° F., 360° F., 360° F., and 340° F., respectively.

The resulting film was collected at a speed of 40 rpm on the core extruder and 9 rpm on the skin extruder. However, it was observed that the film was very sticky and could not be readily separated.

EXAMPLE 24

A two-layered, co-extruded film was formed as described in Example 23, except that the core layer contained 60 wt. % plasticized Glucosol 800 (containing 70 wt. % Glucosol 800 and 30 wt. % sorbitol), 30 wt. % plasticized polyvinyl alcohol (70% wt. % Elvanol 51-05 and 30 wt. % sorbitol), and 10 wt. % Ecoflex® F BX 7011 resin. The target weight of the layers was 8 wt. % of the film for the skin layer and 92 wt. % of the film for the core layer. It was observed that the film was very sticky and could not be readily separated.

EXAMPLE 25

A two-layered, co-extruded film was formed as described in Example 23, except that the skin layer contained 100 wt. % Bioplast™ 106/02 (Biotec), which includes potato starch and a biodegradable copolyester. The three (3) zones and feedblock of the skin extruder was set at temperatures of 320° F., 320° F., 320° F., and 340° F., respectively, and the three (3) zones and feedblock of the core extruder was set at 320° F., 360° F., 360° F., and 340° F., respectively. The target weight of the layers was 8 wt. % of the film for the skin layer and 92 wt. % of the film for the core layer. The resulting film was collected at a speed of 17.6 rpm on the skin extruder. The film was not observed to be sticky and was readily collected and separated.

EXAMPLE 26

A two-layered, co-extruded film was formed as described in Example 25, except that the target weight of the layers was 19 wt. % of the film for the skin layer and 81 wt. % of the film for the core layer.

EXAMPLE 27

The blend was formed using a ZSK-57 twin screw extruder that had a screw length of 2160 mm. The blend contained 41 wt. % Glucosol 800, 16 wt. % polyvinyl alcohol (Elvanol 51-05), 20 wt. % glycerin, 2 wt. % surfactant, and 20 wt. %

Ecoflex® F BX 7011 resin. The temperatures of the extrusion zones were 219° F., 278° F., 350° F., 344° F., 346° F., 313° F., and 293° F. The screw speed was 300 rpm, the melt temperature was 333° F., and the die temperature was 319° F. The blend was produced at a rate of 200 lbs/hr. The film properties of the resin are provided below:

| Thickness (mil) | | Peak Stress (MPa) | | Strain at Break (%) | | Modulus (MPa) | | Energy per Volume at Break (J/cm³) | |
|---|---|---|---|---|---|---|---|---|---|
| MD | CD | MD | CD | MD | CD | MD | CD | MD | CD |
| 1.03 | 1.23 | 9.1 | 6.0 | 433 | 238 | 4.3 | 9.0 | 26 | 8.8 |
| 1.35 | 0.9 | 7.6 | 5.2 | 442 | 179 | 12 | 7.1 | 22 | 6 |

The top row of the data were obtained under ambient conditions, and the bottom row of data was obtained after conditioning at 22° C. and 50% relative humidity for 24 hrs.

EXAMPLE 28

A mixture of Glucosol 800, Elvanol 51-05, and Excel P-40S (42/16/2) was initially prepared using a Hobart mixer. The mixture was fed by a gravimetric feeder (K-Tron America, Pitman, N.J.) at the feed throat of ZSK-30 twin screw extruder (Werner and Pfleiderer Corporation, Ramsey, N.J.). The extruder diameter was 30 mm with the length of the screws up to 1328 mm. The extruder had 14 barrels, numbered consecutively 1~14 from the feed hopper to the die. The first barrel #1 received the mixture of starch, Elvanol 51-05, and surfactant at 12 lbs/hr when the extruder was heated to 100° C., 121° C., 144° C., 155° C., 154° C., 150° C., and 135° C. from zone 1 to 7. Glycerin was pumped into the second barrel #2 at 3.8 lbs/hr using an Eldex pump, and Ecoflex® F BX 7011 resin was fed separately at 4 lbs/hr using another K-Tron feeder. The screw was set to rotate at 150 rpm. The melting temperature was 150° C., the melt pressure was 220 psi, and the torque was 32 to 35%. The vent was opened at the end of the extruder to release moisture. The die used to convert starch to thermoplastic starch has 3 openings of 5 mm in diameter which were separated by 3 mm. The thermoplastic starch strands were cooled on a conveyer belt and then pelletized.

The resulting blend contained 17 wt. % glycerin, 20 wt. % Ecoflex® F BX 7011 resin, 44 wt. % of Glucosol 800, 17 wt. % Elvanol 51-05, and 2 wt. % Excel P40S.

EXAMPLE 29

Two-layer film casting was carried out using the same equipment setup described in Example 18. The water-dispersible core layer was made from the material of Example 28 and the water-barrier skin layer was made from the material of Example 17. The distribution of the core/skin in the film was 90/10 (core/skin). The processing temperature for the core extruder was 320° F., 360° F., 360° F., and 340° F. from three heating zones and feedblock, respectively. For the skin extruder, the temperature profile was 340° F., 340° F., 324° F., and 340° F., respectively. The die temperature was 335° F. The film was processed at 30 ft/min. The core extruder feeding rate was fixed at 55 rpm, while skin extruder feeding rate was adjusted to achieve the ratio of 90/10.

The film mechanical properties were tested using MTS Synergie 200 (MTS Ststems Corporation, Rockford, Ill.). The samples were conditioned at 70° F. and 50% humidity overnight and prepared for testing by taking a portion of the film and cutting five dog-bone shaped samples in each direction, i.e., machine direction (MD) and cross direction (CD). The gauge length of each dog-bone was 18 mm, the width in the center was 3 mm, and the thickness varied around 1 mil. Each dog-bone was tested separately. During the test, samples were stretched at a crosshead speed of 5.0 inches/minute until breakage occurred. The computer program TestWorks 4 collected data points during the testing and generated a stress (MPa) versus strain (%) curve from which a variety of properties were determined: modulus, peak stress, elongation, and toughness. The film mechanical property data is listed below:
Modulus: MD=24 MPa, CD=16 MPa;
Peak stress: MD=17 MPa, CD=3 MPa;
Strain at Break: MD=196%, CD=151%;
Total Energy to Break: MD=21 J/cm³, CD=4 J/cm³.

EXAMPLE 30

A film was formed as described in Example 29, except core/skin weight ratio was 85/15. The mechanical properties of the film are set forth below:
Modulus: MD=31 MPa, CD=13 MPa;
Peak stress: MD=16 MPa, CD=3 MPa;
Strain at Break: MD=173%, CD=151%;
Total Energy to Break: MD=18 J/cm³, CD=3 J/cm³.

EXAMPLE 31

Two-layer film casting was carried out using the same equipment setup described in Example 18. The water-dispersible core layer was made from the material of Example 27 and the water-barrier skin layer was made from 100 wt. % Bioplast™ 106/02 (Biotec). The distribution of the core/skin in the film was 80/20 (core/skin). The processing conditions are the same as used in Example 29. The mechanical properties of the film are set forth below:
Modulus: MD=22 MPa, CD=32 MPa;
Peak stress: MD=15 MPa, CD=3 MPa;
Strain at Break: MD=136%, CD=93%;
Total Energy to Break: MD=12 J/cm³, CD=2 J/cm³.

EXAMPLE 32

A twin-screw extruder of ZSK-70 (Werner and Pfleiderer Corporation, Ramsey, N.J.) was used to make a starch-based blend to serve as a core in the two-layer film. The extruder has shaft length of 2970 mm with diameter of 70.5 mm. A mixture of Glucosol 800 (96%) and Excel P40S (4%) was made and fed into the first zone, which resulted in 51% in the final blend. Elvanol 51-05 (19%) and Ecoflex® F BX 7011 (20%) were fed into the same barrel, separately. Glycerin (10%) was pumped into the third zone. The processing temperatures from zones 1 to 10 (die) were set at 200° F., 280° F., 300° F., 300° F., 300° F., 300° F., 270° F., 270° F., 270° F., and 300° F. Actual temperatures from zones 1 to 10 (die) were 216° F., 292° F., 311° F., 285° F., 303° F., 262° F., 284° F., 257° F., 272° F., and 295° F. The melting temperature was 332° F. The screw rotational speed was 200 rpm and the total output was 300 lbs/hr. A total material output at 400 lbs/hr was also run on ZSK-70 with an increase of the screw rotational speed to 400 rpm. Other parameters were the same during the processing the starch-based blend.

EXAMPLE 33

A twin-screw extruder of ZSK-70 (Werner and Pfleiderer Corporation, Ramsey, N.J.) was used to make a starch-based blend to serve as a core in the two-layer film. The extruder has shaft length of 2970 mm with diameter of 70.5 mm. Elvanol 51-05 (75%) was fed into the first zone, 2sst $CaCO_3$ (Omya, Inc., 15%) was fed into the same barrel. The material feeding independently eliminated the pre-mixing step. Glycerin (10%) was pumped into the third zone. The processing temperatures from zones 1 to 10 (die) were set at 250° F., 280° F., 400° F., 400° F., 400° F., 400° F., 360° F., 360° F., and 380° F. Actual temperatures from zones 1 to 10 (die) were 192° F., 283° F., 405° F., 326° F., 401° F., 406° F., 369° F., 366° F., 361° F., and 378° F. The melting temperature was 413° F. The screw rotational speed was 200 rpm and total output was 380 lbs/hr. At the same extruder running conditions, Celvol 523S (polyvinyl alcohol) was also tried, but material buildup was observed in the throat. Rotational screw speed was also increased to 350 rpm due to the fact that because Celvol 523S was a fine powder, while Elvanol 51-05 was more granular. Nevertheless, glycerin still pooled in the extruder.

EXAMPLE 34-36

The plasticized polyvinyl alcohol from Example 33 was used to make two layered films. Example 34 contained 80 wt. % of dried plasticized polyvinyl alcohol from Example 33 (core layer) and 20 wt. % of Bioplast™ 106/02 (skin layer), Example 35 contained 80 wt. % of undried plasticized polyvinyl alcohol from Example 33 (core layer) and 20 wt. % of Bioplast™ 106/02 (skin layer), and Example 36 contained 86 wt. % of undried plasticized polyvinyl alcohol from Example 33 (core layer) and 14 wt. % of Bioplast™ 106/02 (skin layer). The target thickness of the films was 1 mil. A 1.25" Killion extruder (with melt pump) was used to supply the core layer. The processing temperatures for zones 1 to 5 (melt pump) of the extruder were set at 330° F., 350° F., 350° F., 350° F., and 350° F. for Example 34; 350° F., 350° F., 360° F., 360° F., and 360° F. for Example 35; and 350° F., 350° F., 360° F., 360° F., and 360° F. for Example 36. The screw rotational speed was 30 rpm, 27 rpm, and 28 rpm for Examples 34-36, respectively. A 28 mm Leistritz twin screw extruder (without melt pump) was used to supply the skin layer. For each of the Examples, the processing temperatures for zones 1 to 10 (die) of the extruder were set at 70° C., 140° C., 150° C., 160° C., 165° C., 165° C., 165° C., 165° C., 165° C., and 165° C. The screw rotational speed was 100 rpm.

The film mechanical properties for these samples are also shown below. Two-layer film mechanical properties from Example 34:
  Modulus: MD=194 MPa, CD=163 MPa;
  Peak stress: MD=19 MPa, CD=10 MPa;
  Strain at Break: MD=213%, CD=87%;
  Total Energy to Break: MD=29 J/cm$^3$, CD=7 J/cm$^3$.
Two-layer film mechanical properties from Example 35:
  Modulus: MD=206 MPa, CD=196 MPa;
  Peak stress: MD=32 MPa, CD=21 MPa;
  Strain at Break: MD=190%, CD=269%;
  Total Energy to Break: MD=40 J/cm$^3$, CD=42 J/cm$^3$.
Two-layer film mechanical properties from Example 36:
  Modulus: MD=162 MPa, CD=148 MPa;
  Peak stress MD=40 MPa, CD=22 MPa;
  Strain at Break: MD=216%, CD=258%;
  Total Energy to Break: MD=52 J/cm$^3$, CD=41 J/cm$^3$.

EXAMPLE 37

A two-layer blown film was manufactured using 92 wt. % of the blend of Example 32 as the water-dispersible core layer and 8 wt. % of 100 wt. % Bioplast™ 106/02 (Biotec) as the water-barrier skin layer. The setup temperature was 340° F., 350° F., 360° F., and 345° F. from zone 1 to zone 3 and adaptor, respectively. The melting temperature ranged from 320° F. to 350° F., and melting pressure changed from 1447 to 4300 psi. Screw rotational speed varied 14 rpm for Bioplast™ 106/02 to about 40 rpm for the blend of Example 32. The ring size was 14 inches, the film bubble diameter was 34 inches, and the length of the bubble was 45 feet, where the film thickness is about 1.5 mils. The mechanical properties are set forth below:
  Modulus: MD=26 MPa, CD=19 MPa;
  Peak stress: MD=9 MPa, CD=3 MPa;
  Strain at Break: MD=234%, CD=200%;
  Total Energy to Break: MD=21 J/cm$^3$, CD=4 J/cm$^3$ This film was also subjected to aerobic and anaerobic biodisintegration testing as referenced above. Both tests results in 96% disintegration after 21 days.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. An absorbent article that comprises:
a liquid permeable topsheet;
a generally liquid impermeable backsheet; and
an absorbent core positioned between the backsheet and the topsheet;
wherein the backsheet includes a biodegradable and flushable film comprising a water-dispersible core layer and a water-barrier skin layer positioned adjacent to the water-dispersible core layer, the water-dispersible core layer constituting from about 50 wt. % to about 99 wt. % of the film and the water-barrier skin layer constituting from about 1 wt. % to about 50 wt. % of the film,
wherein the water-dispersible core layer comprises from about 10 wt. % to about 40 wt. % of a partially hydrolyzed polyvinyl alcohol, from about 30 wt. % to about 70 wt. % of a chemically modified starch, and from about 10 wt. % to about 40 wt. % of a synthetic biodegradable copolyester; and
wherein the water-barrier skin layer comprises from about 20 wt. % to about 50 wt. % of a chemically modified starch and from about 50 wt. % to about 80 wt. % of a synthetic biodegradable copolyester, wherein the film has a percent elongation at break in the cross-machine direction ranging from 5% to 151%.

2. The absorbent article of claim 1, wherein the chemically modified starch and the synthetic biodegradable polyester constitute from about 80 wt. % to 100 wt. % of the polymer content of the water-barrier skin layer.

3. The absorbent article of claim 1, wherein the chemically modified starch polymer includes potato starch or a derivative thereof, corn starch or a derivative thereof, or mixtures of the foregoing.

4. The absorbent article of claim 1, wherein the chemically modified starch polymer includes a hydroxyalkyl starch.

5. The absorbent article of claim 1, wherein the chemically modified starch polymer has a weight average molecular weight of from about 5,000,000 to about 25,000,000 grams per mole.

6. The absorbent article of claim 1, wherein the synthetic biodegradable copolyester has a glass transition temperature of about 0° C. or less and a melting point of from about 50° C. to about 180° C.

7. The absorbent article of claim 1, wherein the synthetic biodegradable copolyester includes an aliphatic-aromatic copolyester.

8. The absorbent article of claim 7, wherein the synthetic biodegradable copolyester includes polybutylene adipate terephthalate.

9. The absorbent article of claim 1, wherein the water-barrier skin layer further contains a plasticizer.

10. The absorbent article of claim 1, wherein the water-dispersible core layer further contains a plasticizer.

11. The absorbent article of claim 1, wherein the water-dispersible core layer further contains a filler.

12. The absorbent article of claim 11, wherein fillers constitute from about 1 wt. % to about 30 wt. % of the water-dispersible core layer.

13. The absorbent article of claim 1, wherein the film has a thickness of about 50 micrometers or less.

14. The film of claim 1, wherein the film has a percent elongation at break in the machine direction of from about 60% to 196%.

15. The film of claim 1, wherein the film has a percent elongation at break in the machine direction and cross-machine direction of less than 130%.

16. A biodegradable and flushable film having a thickness of about 50 micrometers or less, the film comprising:
  a water-dispersible core layer that comprises from about 10 wt. % to about 40 wt. % of a partially hydrolyzed vinyl alcohol polymer, from about 30 wt. % to about 70 wt. % of a chemically modified starch, and from about 10 wt. % to about 40 wt. % of a synthetic biodegradable copolyester; and
  a water-barrier skin layer positioned adjacent to the water-dispersible core layer, the core layer constituting from about 50 wt. % to about 99 wt. % of the film and the skin layer constituting from about 1 wt. % to about 50 wt. % of the film, wherein the water-barrier skin layer comprises from about 20 wt. % to about 50 wt. % of a chemically modified starch and from about 50 wt. % to about 80 wt. % of a synthetic biodegradable copolyester, wherein the film has a percent elongation at break in the cross-machine direction ranging from 5% to 151%.

17. The film of claim 16, wherein the chemically modified starch polymer includes a hydroxyalkyl starch.

18. The film of claim 16, wherein the synthetic biodegradable copolyester includes an aliphatic-aromatic copolyester.

19. The film of claim 16, wherein the water-dispersible core layer further contains a filler.

20. The film of claim 19, wherein fillers constitute from about 1 wt. % to about 30 wt. % of the water-dispersible core layer.

21. A pouch, wrap, or bag comprising the water-sensitive biodegradable film of claim 16.

22. The film of claim 16, wherein the film has a percent elongation at break in the machine direction of from about 60% to 196%.

23. The film of claim 16, wherein the film has a percent elongation in the machine direction and cross-machine direction of less than 130%.

* * * * *